United States Patent
Taniguchi et al.

(10) Patent No.: US 10,222,601 B2
(45) Date of Patent: *Mar. 5, 2019

(54) MICROSCOPE, FOCUSING UNIT, FLUID HOLDING UNIT, AND OPTICAL UNIT

(71) Applicant: RIKEN, Saitama (JP)

(72) Inventors: Yuichi Taniguchi, Saitama (JP); Kazuya Nishimura, Saitama (JP)

(73) Assignee: RIKEN, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/854,884

(22) Filed: Dec. 27, 2017

(65) Prior Publication Data

US 2018/0120551 A1 May 3, 2018

Related U.S. Application Data

(63) Continuation of application No. 14/781,625, filed as application No. PCT/JP2014/059883 on Apr. 3, 2014, now Pat. No. 9,880,378.

(30) Foreign Application Priority Data

Apr. 5, 2013 (JP) .................................. 2013-079956

(51) Int. Cl.
*G02B 21/16* (2006.01)
*G02B 21/33* (2006.01)
(Continued)

(52) U.S. Cl.
CPC ......... *G02B 21/16* (2013.01); *G01N 21/6458* (2013.01); *G02B 21/0076* (2013.01);
(Continued)

(58) Field of Classification Search
CPC .... G02B 21/0088; G02B 21/06; G02B 21/16; G02B 21/26; G02B 21/33; G02B 21/0076;
(Continued)

(56) References Cited

U.S. PATENT DOCUMENTS 5,144,478 A 9/1992 Toshimitsu
5,684,627 A 11/1997 Ganser et al.
(Continued)

FOREIGN PATENT DOCUMENTS

EP 1855140 A1 11/2007
EP 1865354 A1 12/2007
(Continued)

OTHER PUBLICATIONS

International Search Report PCT/ISA/210 for International Application No. PCT/JP2014/059883 dated Jun. 24, 2014.
(Continued)

*Primary Examiner* — Frank G Font
(74) *Attorney, Agent, or Firm* — Harness, Dickey & Pierce, P.L.C.

(57) ABSTRACT

A microscope includes: a sample placement part having a placement surface on which to place a sample and a bottom face opposite to the placement surface; an observation lens; and an optical unit for generating sheet light and use of the microscope. The microscope of an embodiment is arranged such that the sheet light enters the sample placement part from the bottom face and passing through the sample placement part to irradiate the sample, and fluorescence from the sample passes through the sample placement part toward the bottom face to be received by the observation lens. The microscope can, with this arrangement, utilize the advantages of a SPIM, and allows observation of a sample which observation is free from a restriction of the size of a sample.

12 Claims, 19 Drawing Sheets

(51) Int. Cl.

| | | |
|---|---|---|
| *G02B 21/26* | (2006.01) | |
| *G02B 21/08* | (2006.01) | |
| *G02B 21/24* | (2006.01) | |
| *G02B 21/00* | (2006.01) | |
| *G01N 21/64* | (2006.01) | |
| *G02B 21/10* | (2006.01) | |

(52) U.S. Cl.
 CPC ......... *G02B 21/0088* (2013.01); *G02B 21/08* (2013.01); *G02B 21/10* (2013.01); *G02B 21/24* (2013.01); *G02B 21/26* (2013.01); *G02B 21/33* (2013.01)

(58) Field of Classification Search
 CPC ........ G02B 21/08; G02B 21/10; G02B 21/24; G01N 21/6458
 USPC .......................................... 359/385, 391–394
 See application file for complete search history.

(56) References Cited

U.S. PATENT DOCUMENTS

| | | | |
|---|---|---|---|
| 7,277,566 | B2 | 10/2007 | Miyawaki et al. |
| 2006/0033987 | A1 | 2/2006 | Stelzer et al. |
| 2007/0109633 | A1 | 5/2007 | Stelzer |
| 2009/0225413 | A1 | 9/2009 | Stelzer et al. |
| 2010/0027109 | A1 | 2/2010 | Liebel et al. |
| 2010/0067104 | A1* | 3/2010 | Lippert .................. G02B 21/26 359/391 |
| 2010/0177381 | A1* | 7/2010 | Lippert .................. G02B 21/26 359/398 |
| 2010/0201784 | A1 | 8/2010 | Lippert et al. |
| 2011/0149394 | A1 | 6/2011 | Wadell et al. |
| 2011/0304723 | A1 | 12/2011 | Betzig |
| 2012/0098949 | A1 | 4/2012 | Knebel et al. |
| 2012/0099190 | A1 | 4/2012 | Knebel et al. |
| 2012/0206798 | A1 | 8/2012 | Knop et al. |
| 2013/0094755 | A1 | 4/2013 | Lippert et al. |
| 2014/0042339 | A1 | 2/2014 | Stelzer et al. |
| 2015/0286042 | A1 | 10/2015 | Hilbert et al. |
| 2015/0309294 | A1* | 10/2015 | Stelzer .................. G02B 21/06 359/370 |

FOREIGN PATENT DOCUMENTS

| | | |
|---|---|---|
| JP | 2003185930 A | 7/2003 |
| JP | 2005003909 A | 1/2005 |
| JP | 2006509246 A | 3/2006 |
| JP | 2006276663 A | 10/2006 |
| JP | 2008000863 A | 1/2008 |
| JP | 2010540994 A | 12/2010 |
| JP | 2012093757 A | 5/2012 |
| JP | 2012108491 A | 6/2012 |
| WO | WO-2007124437 A2 | 11/2007 |
| WO | WO-2008/028475 A2 | 3/2008 |
| WO | WO-2008/137746 A1 | 11/2008 |

OTHER PUBLICATIONS

International Preliminary Report on Patentability dated Oct. 6, 2015.
Tokunaga, M. et al., "Highly inclinged thin illumination enables clear single-molecule imaging in cells," Nature Methods, 5, pp. 159-161, 2008.
Huisken, J. et al., "Optical Sectioning Deep Inside Live Embryos by Selective Plane Illumination Microscopy," Science, vol. 305, pp. 1007-1009, 2004.
Anonymous, "Inverted microscope," Wikipedia, the free encyclopedia, Oct. 13, 2012.
Supplementary Partial European Search Report of corresponding EP Application No. 14778778.2 dated Jan. 12, 2017.
Search Report for Corresponding European Patent Application No. 14778778.2 dated Jun. 16, 2017.
Machine translation of JP 2003-185930 A downloaded from "https://www4.j-platpat.inpit.go.jp/eng/tokujitsu/tkbs_en/TKBS_EN_GM101_Top.action" on Jun. 5, 2017.
Machine translation of "JP 2005-003909 A" downloaded from "https://www4.j-platpat.inpit.go.jp/eng/tokujitsu/tkbs_en/TKBS_EN_GM101_Top.action" on Jun. 5, 2017.
C. Dunsby, "Optically sectioned imaging by oblique plane microscopy", Optics Express, vol. 16, No. 25, pp. 20306-20316, Nov. 24, 2008.
Office Action for U.S. Appl. No. 14/781,625 dated Jun. 9, 2017.
Notice of Allowance for U.S. Appl. No. 14/781,625 dated Sep. 22, 2017.

* cited by examiner

MICROSCOPE, FOCUSING UNIT, FLUID HOLDING UNIT, AND OPTICAL UNIT

CROSS-REFERENCE TO RELATED APPLICATIONS

This U.S. non-provisional application is a continuation of U.S. application Ser. No. 14/781,625 filed on Oct. 1, 2015, which is the U.S. National Phase application of PCT Application No. PCT/JP2014/059883 filed on Apr. 3, 2014, which claims priority to Japanese Application No. 2013-079956 filed on Apr. 5, 2013, the contents of each of which are incorporated herein by reference.

TECHNICAL FIELD

The present invention relates to a microscope, a focusing device for use in a microscope, a fluid holding device for use in a microscope, and an optical unit for use in a microscope.

BACKGROUND ART

There has been known a microscope that irradiates an observation plane of a sample locally with light and that receives fluorescence radiated from the sample. The microscope, with such an arrangement, allows an observation of sectioned planes of a sample. Such a microscope, which is capable of preventing light from illuminating that portion of a sample which is not an observation plane, can reduce the background during the observation of the sample and can also reduce, for example, harmful action to a sample or attenuation of fluorescence that are caused by irradiation of the sample with excitation light.

Patent Literatures 1 and 2 and Non Patent Literature 1 each disclose a highly inclined and laminated optical sheet microscopy for an optical microscope, with which technique illumination light is refracted with use of an objective lens to irradiate a sample in an oblique direction with respect to the optical axis of the objective lens. FIG. 18 shows enlarged views of part of an optical microscope that uses the highly inclined laminated optical sheet microscopy of Patent Literature 1. In a case where an optical microscope is arranged such that illumination light enters a sample in a direction so angled as to be close to perpendicular to the optical axis of the objective lens as illustrated in FIG. 18, the optical microscope can irradiate a sample with a thin layer-shaped light having a small thickness along the direction of the optical axis of the objective lens. According to Patent Literature 1, the optical microscope is capable of continuously capturing an image of a sample while moving the focal position of the objective lens to produce a three-dimensional image at a high resolution. Patent Literature 1 discloses in particular that the optical microscope is capable of imaging at a single-molecule level.

The technique disclosed in Patent Literature 1 may serve to adjust the position on an objective lens at which position illumination light enters the objective lens, so that the angle θ between optical axes of illumination light refracted and the objective lens is close to 90 degrees. The technique, however, does not allow the angle θ to be exactly 90 degrees. Thus, the optical axis of illumination light is not parallel to the observation plane of the objective lens. This arrangement results in an image being ununiformly out of focus to varying degrees over the observation plane, the image thus having decreased quality evenness. Further, the above arrangement lets illumination light illuminate a region of a sample which region is other than the observation plane, and thus increases the background, with the result of a fluorescence image having a decreased resolution. In particular, in a case of producing a three-dimensional image, such an image will have a low resolution along the direction parallel to the optical axis of the objective lens.

Non Patent Literature 2 discloses SPIM (selective plane illumination microscope), which irradiates a sample with a thin layer-shaped sheet light, collects radiated fluorescence with use of an objective lens having an optical axis perpendicular to the optical axis of the sheet light, and forms an image of the collected fluorescence with use of a camera. In a case of observing a sample with use of the SPIM of Non Patent Literature 2, the SPIM rotates agarose gel in which the sample is embedded and thus irradiates the sample with sheet light from various angles, and captures an image of the sample with use of a camera. FIG. 19 is a diagram schematically illustrating a part of the microscope of Non Patent Literature 2 on which part a sample is placed. Patent Literature 3 discloses that in a case of collecting light with use of an illumination lens and irradiating a sample with the collected light in the form of layer-shaped sheet light, the sheet light has a thickness along the direction parallel to the optical axis of the objective lens which thickness depends on the numerical aperture of the illumination lens. This disclosure indicates that in a SPIM, increasing the numerical aperture of the illumination lens can reduce the thickness of sheet light and can thereby reduce the background.

Patent Literatures 4 to 6 each similarly disclose a microscope that collects fluorescence from a sample with use of an objective lens having an optical axis perpendicular to the optical axis of sheet light and that thereby produces a three-dimensional image of the sample.

In a case of irradiating a sample with sheet light in the direction perpendicular to the optical axis of an objective lens as with the microscopes disclosed in Patent Literatures 3 to 6 and Non Patent Literature 2, it is possible to reduce the background and, as a result, obtain a high resolution.

CITATION LIST

Patent Literature 1
Japanese Patent Application Publication, Tokukai, No. 2003-185930 A (Publication Date: Jul. 3, 2003)
Patent Literature 2
Japanese Patent Application Publication, Tokukai, No. 2005-3909 A (Publication Date: Jan. 6, 2005)
Patent Literature 3
Japanese Translation of PCT International Application, Tokuhyo, No. 2006-509246 (Publication Date: Mar. 16, 2006)
Patent Literature 4
Japanese Patent Application Publication, Tokukai, No. 2012-93757 A (Publication Date: May 17, 2012)
Patent Literature 5
Japanese Patent Application Publication, Tokukai, No. 2012-108491 A (Publication Date: Jun. 7, 2012)
Patent Literature 6
U.S. Patent Application Publication No. US2011/0304723 (Publication Date: Dec. 15, 2011)
Non Patent Literature 1
M. Tokunaga et al., Nature Methods, 5, pp. 159-161, 2008
Non Patent Literature 2
Jan Huisken et al., SCIENCE 2004 VOL 305, pp. 1007-1009, 2004

SUMMARY OF INVENTION

Technical Problem

The existing SPIM allows observation of a sample (for example, a cultured cell) embedded in agarose gel as with the SPIM of Non Patent Literature 2 illustrated in FIG. 19. A sample such as a cell in a culture solution cultured in a petri dish is thus difficult to observe while the sample is being cultured. This means that conventional SPIMs have only limited measurement applications. Further, since a cultured cell embedded in gel may behave differently from when the cell is in a culture medium, conventional SPIMs are not suitable for continuous observation of a living cell. In addition, conventional SPIMs, which require a sample to be embedded in a gel having a predetermined volume, are problematically limited in terms of the size of a sample.

In view of that, the inventors of the present invention have studied the possibility of not embedding a sample in gel and observing the sample placed on a flat cover slip, similarly to a biological sample for normal microscope observation, with use of a SPIM configuration. In this case, a detection objective lens may be oriented perpendicularly to the surface of the cover slip so that a fluorescence image will not be influenced by aberration that occurs when fluorescence passes through the cover slip.

Sheet light is, however, wide along the direction parallel to the optical axis of the objective lens. Thus, in a case where light irradiates a region near the cover slip, a portion of such light passes through the top and bottom faces and end faces of the cover slip. Individual light beams thus travel on optical paths different from one another due to refraction, reflection, and/or the like, so that the sheet illumination has decreased quality. Sheet light irradiating a sample thus has an increased thickness, with the result of a failure to sufficiently utilize the advantages of a SPIM.

The present invention has been accomplished in view of the above problem. It is an object of the present invention to provide a microscope having high resolution which microscope can utilize the advantages of a SPIM, allows observation of a sample which observation is free from a restriction of the size of a sample, and allows observation of, for example, a cell in a culture solution or a sample on a cover slip and a member included in the microscope.

Solution to Problem

In order to solve the above problem, a microscope of the present invention is a microscope, including: a sample placement part having a placement surface on which to place a sample and a bottom face opposite to the placement surface; an observation lens for receiving fluorescence from the sample; and an optical unit for generating sheet light traveling in a direction parallel to an observation plane of the observation lens, the sheet light entering the sample placement part from the bottom face and passing through the sample placement part to irradiate the sample, the fluorescence passing through the sample placement part toward the bottom face to be received by the observation lens.

The above arrangement allows an observation to be carried out without the need to embed a sample on the sample placement part in gel and in a state where the advantages of a SPIM are utilized. Further, since the above arrangement allows the observation lens to be so disposed as to be opposite to a sample with respect to the sample placement part, the size of a sample placed on the sample placement part is not limited to a size within the range of the working distance of the observation lens.

In a case where a SPIM observation is to be carried out with an objective lens placed on an axis perpendicular to a surface of the sample placement part, sheet light will interfere with the sample placement part, with the result of a decrease in the quality of the sheet illumination. In contrast, the microscope of the present invention, which allows all the light to enter the observation plane from the bottom face of the sample placement part, makes it possible to successfully control the thickness of sheet light even in a case where a sample near the sample placement part is to be observed.

The microscope of the present invention may further include: a focusing mechanism for adjusting a relative positional relationship between the observation lens and the sample, wherein the focusing mechanism changes the positional relationship along a first direction, which is parallel to an optical axis of the observation lens, and a second direction and a third direction, which define the placement surface.

With the above arrangement, adjusting the relative positional relationship between the observation lens and the sample placement part along the second direction and third direction can change the observed field of view without changing the distance between the sample placement part and the observation lens. The above arrangement can also prevent unnecessary contact between the sample placement part and the observation lens while the microscope changes the observed field of view. At the same time, adjusting the relative positional relationship between the observation lens and the sample placement part along the first direction can achieve focusing without changing the observed field of view. The above arrangement thus makes it possible to capture images of a sample sectioned on a plurality of observation planes perpendicular to the first direction to produce a three-dimensional image of the sample at a high resolution.

The microscope of the present invention may further include: a fluid holding device for holding fluid between the observation lens and the sample placement part, wherein: the fluid holding device includes a connection section for connection to the observation lens; an end face so designed as to face the bottom face; a transmission window through which the sheet light enters the sample placement part; and a fluid holding section for holding fluid inside itself; and in a state where the fluid holding device is connected to the observation lens, the end face is substantially parallel to the bottom face, the sheet light passes through the transmission window and then through the fluid holding section to irradiate the sample, and the fluorescence passes through the fluid holding section to be received by the observation lens.

For measurement at a higher resolution and higher sensitivity, the microscope of the present invention may preferably be arranged such that the observation lens is an immersion lens; and the fluid holding section is filled with a liquid corresponding to the immersion lens.

In a case where an immersion lens is used as the observation lens, a liquid corresponding to the immersion lens should be present between the bottom face of the sample placement part and the lens. The microscope of the present invention is arranged such that the bottom face of the sample placement part is not perpendicular to the optical axis of the observation lens. Thus, it may not be easy to hold the liquid corresponding to the immersion lens between the bottom face and the lens without moving (or changing the shape of) the liquid when changing the relative positional relationship between the observation lens and the sample placement part.

With the above arrangement, however, the fluid holding device can hold the liquid between the observation lens and the sample placement part in a state where the surface shape of the liquid is maintained.

The microscope of the present invention may preferably be arranged such that the fluid holding section is filled with water; and the sample placement part has a refractive index of 1.28 to 1.38.

The microscope is arranged such that the observation lens has an optical axis not orthogonal to the placement surface.

In such a case, left-right asymmetric aberration will emerge depending on the difference between the refractive index of the liquid filling the fluid holding section and the refractive index of the sample placement part. However, in a case where the fluid holding section is filled with water, and the sample placement part has a refractive index of 1.28 to 1.38, which is equivalent to the refractive index of water, it is possible to reduce aberration significantly and form a stable image.

The microscope of the present invention may preferably be arranged such that the observation plane and the placement surface form an angle within a range from 1 degree to 75 degrees.

The angle between the observation plane, which is parallel to the traveling direction of sheet light, and the placement surface needs to allow generation of sheet light having a sufficient thinness. The angle between the observation plane and the placement surface is thus preferably so adjusted as to fall within the range from 1 degree to 75 degrees in correspondence with the purpose of measurement.

The microscope of the present invention may preferably be arranged such that the optical unit includes an optical surface plate having a surface on which one or more optical elements for generating the sheet light are disposed; and the optical surface plate is oriented so that the surface of the optical surface plate is parallel to the observation plane.

With the above arrangement, the one or more optical elements are disposed on the surface of the optical surface plate. This allows the optical unit to generate sheet light traveling in a direction parallel to the observation plane.

The microscope of the present invention may preferably be arranged such that the one or more optical elements include a light source, a light converging element, and a light distributing element; and the one or more optical elements optionally further include a wedge prism.

In order to solve the above problem, a focusing device of the present invention is a focusing device for, in a case where a sample on a placement surface of a sample placement part is to be observed, adjusting a relative positional relationship between an observation lens having an optical axis not orthogonal to the placement surface and the sample, the focusing device including: a first stage for changing the relative positional relationship between the observation lens and the sample along a first direction, which is parallel to the optical axis of the observation lens; a second stage for changing the relative positional relationship between the observation lens and the sample along a second direction and a third direction, which define the placement surface; and a jig for fixing the sample placement part, the jig being attached to one of the first stage and the second stage, the one of the first stage and the second stage, to which one the jig is attached, being placed on one of the first stage and the second stage to which the one jig is not attached.

In order to solve the above problem, a fluid holding device of the present invention is a fluid holding device for holding fluid between an observation lens and a sample placement part having a placement surface on which to place a sample to be observed and a bottom face so designed to be opposite to the placement surface, the fluid holding device including a connection section for connection to the observation lens; an end face so designed as to face the bottom face; a transmission window through which sheet light enters the sample placement part; a fluid holding section for holding fluid inside itself, in a state where the fluid holding device is connected to the observation lens, the end face being substantially parallel to the bottom face, the sheet light from an optical unit passing through the transmission window and then through the fluid holding section to irradiate the sample, and fluorescence from the sample passing through the fluid holding section to be received by the observation lens.

In order to solve the above problem, an optical unit of the present invention is an optical unit including an optical surface plate having a surface on which one or more optical elements for generating sheet light are placed, the optical surface plate being oriented so that the surface of the optical surface plate is parallel to an observation plane of an observation lens.

Advantageous Effects of Invention

With one mode of the present invention, it is possible to observe a sample on the sample placement part without embedding the sample in gel and in a state where the advantages of a SPIM are utilized. Further, the size of a sample placed on the sample placement part is not limited to a size within the range of the working distance of the observation lens. This makes it possible to observe a sample on a transparent planar substrate (sample placement part) similarly to a normal biological microscope, and thus allows observation of, for example, a relatively large biological sample such as an individual mouse.

The above arrangement further prevents a decrease in the quality of sheet light even in a case where an illuminated region is formed near the placement surface of the sample placement part. Thus, even in a case where, for example, a sample adherent to the sample placement part is to be observed, it is possible to observe the sample in a state where the advantages of a SPIM are utilized. For instance, it is possible to directly observe an adherent cell cultured in a petri dish.

DESCRIPTION OF EMBODIMENTS

[Embodiment 1]

The description below deals in detail with an embodiment of the present invention with reference to FIGS. 1 through 5.

Figure 1:
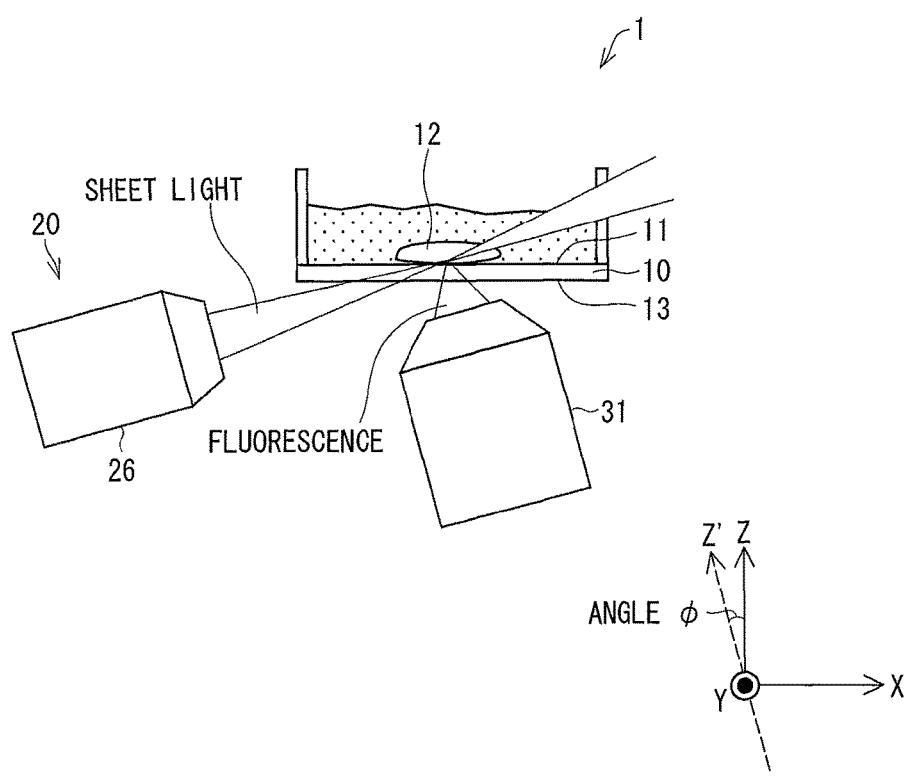
FIG. 1 is a diagram schematically illustrating a main configuration of a microscope of one embodiment of the present invention.

FIG. 1 is a diagram schematically illustrating a main configuration and an optical path of a microscope 1 of the present embodiment. The microscope 1 of the present embodiment, as illustrated in FIG. 1, includes a sample placement part 10 for placing a sample, an optical unit 20 for irradiating the sample with light, and an observation lens 31 for receiving light radiated from the sample. FIG. 1 illustrates an illumination lens 26 as a member of the optical unit 20 which illumination lens 26 is disposed at an opening for emission of light from the optical unit 20.

The sample placement part 10 has a placement surface 11 on which to place a sample 12 and a bottom face 13 opposite to the placement surface 11. The microscope 1 of the present embodiment is, as illustrated in FIG. 1, so configured as to be usable as an inverted microscope such that the illumination lens 26 and the observation lens 31 are so disposed as to be opposite to the sample 12 with respect to the sample placement part 10 (that is, with respect to the plane including the placement surface 11). The sample placement part 10 is entirely or partly made of a light-transmitting material. The sample placement part 10 may be a single cover slip or a bottom face of a culture plate (including a multiwell plate and a microfluidic device) or part of the bottom face. The optical unit 20 irradiates a sample 12 with sheet light through the bottom face 13 of the sample placement part 10. The optical unit 20 emits sheet light, which enters the sample placement part 10 at the bottom face 13 and then exits the sample placement part 10 at the placement surface 11, to finally irradiate the sample 12. The observation lens 31 receives fluorescence radiated from the sample 12 through the bottom face 13 of the sample placement part 10. The sample 12 radiates fluorescence, which enters the sample placement part 10 at the placement surface 11 and then exits the sample placement part 10 at the bottom face 13, to finally be received by the observation lens 31. Further, the illumination lens 26 and the observation lens 31 are so oriented as to have optical axes that are orthogonal to each other on a plane (that is, the X-Z plane in FIG. 1). This arrangement allows the optical unit 20 to irradiate a sample with sheet light traveling in a direction parallel to a surface observed with the observation lens 31. Further, the observation lens 31 has an optical axis in a direction (that is, the Z' direction in FIG. 1) inclined with respect to the direction perpendicular to the placement surface 11 (that is, the Z direction in FIG. 1). FIG. 1 illustrates an embodiment in which the Z direction and the Z' direction are inclined with respect to each other at 15 degrees, and on the X-Z plane, the illumination lens 26 has an optical axis in a direction inclined at $\phi=15$ degrees with respect to the placement surface 11 (that is, the X-Y plane in FIG. 1). This means that the optical axis of the illumination lens 26 is perpendicular to the Y-Z' plane in FIG. 1.

The angle $\phi$ between the Z direction and the Z' direction is not limited to 15 degrees. In a case where the angle between the Z direction and the Z' direction is larger than 15 degrees, increasing the numerical aperture of the illumination lens 26 allows generation of thinner sheet light. Such sheet light will, however, have a smaller light collection depth. In a case where the angle is smaller than 15 degrees, it is possible to reduce the aberration discussed above and effectively utilize the working distance of the objective lens to observe a deeper portion of a sample. In this case, however, only an objective lens with a smaller numerical aperture is usable, so that while sheet light will have a larger light collection depth, the sheet light will have a larger thickness. It is thus preferable to adjust the angle between the optical axis of the illumination lens 26 and the placement surface 11 within the range from 1 degree to 75 degrees in correspondence with the purpose of measurement. In particular, in a case of observing an object at a low magnification (up to ×20), the angle is preferably 1 degree to 10 degrees, in a case of observing object at a high magnification (×40 or higher) over the entire objective lens, the angle is preferably 5 degrees to 20 degrees, and in a case of observing an object at a high magnification (×40 or higher) with a low background, the angle is preferably 35 degrees to 50 degrees.

The microscope 1 of the present embodiment is arranged such that the sheet light has an optical axis inclined with respect to the placement surface 11. This arrangement makes it possible to observe a sample 12 without influencing any other sample 12 on the sample placement part 10 by irradiation with sheet light. The microscope 1 is thus suitable also for measurement that uses a multiwell dish or a microfluidic device.

Figure 2:
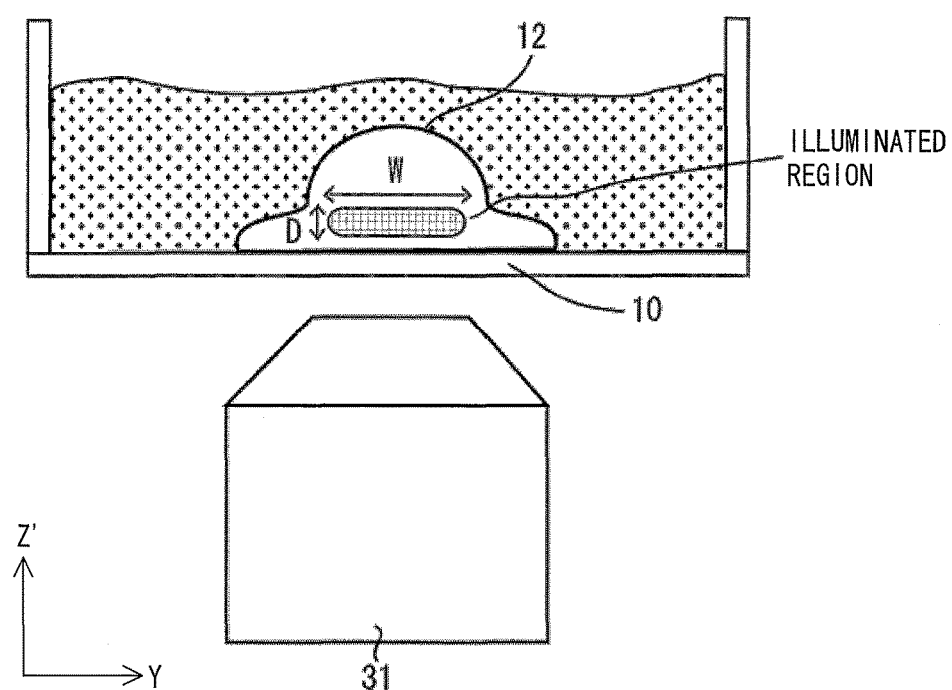
FIG. 2 is a diagram schematically illustrating a main configuration of a microscope of one embodiment of the present invention.

FIG. 2 schematically illustrates cross sections of the sample 12 and the sample placement part 10 on the Y-Z' plane, which includes the optical axis of the observation lens 31, and a region illuminated with sheet light. FIG. 2 shows a Y direction and a Z' direction identical to those shown in FIG. 1.

The illumination lens 26, as described above, emits sheet light. This sheet light forms a thin illumination region on its optical path. As illustrated in FIG. 2, assuming that on the plane perpendicular to the optical axis of the illumination lens 26 (that is, the Y-Z' plane in FIG. 2), the illuminated region has a thickness D and a width W, the illuminated region has, on the Y-Z' plane, a thickness direction identical to the Z' direction in FIG. 2. This means that the observation lens 31 is so oriented as to have an optical axis parallel to the thickness direction of the illuminated region (that is, the Z' direction in FIG. 2). Irradiating a sample 12 with sheet light excites fluorescent material present in the illuminated region of the sample 12, so that the fluorescent material radiates fluorescence. The position of the observation lens 31 (and that of the illumination lens 26, if necessary) is adjusted so that the focus surface (observation plane) of the observation lens 31 is included in the illuminated region, and the observation lens 31 receives fluorescence radiated from the sample 12.

The microscope 1 of the present embodiment allows observation of a sample 12 placed on the sample placement part 10 without the need to embed the sample in a gel and in a state where the following advantages of a SPIM are utilized: (1) A SPIM, which allows observation with weak light irradiation, allows reduction of harmful action to a sample or attenuation of fluorescence; (2) a SPIM is capable of producing a three-dimensional image rapidly; and (3) a SPIM is capable of observing a sample at a high resolution. Further, the microscope 1 of the present embodiment is arranged such that the observation lens 31 is so disposed as to be opposite to a sample 12 with respect to the plane including the placement surface 11. Thus, the area above the sample 12 is open, so that the size of a sample 12 placed on the sample placement part 10 is not limited to a size within the range of the working distance of the observation lens 31. Further, the illumination lens 26 is, as described above, so disposed as to be opposite to a sample 12 with respect to the plane including the placement surface 11, so its sheet light irradiates the sample 12 through the bottom face 13. This arrangement allows all sheet light to enter the observation plane from the bottom face 13 of the sample placement part 10, and thus allows the thickness of sheet light to be controlled successfully even in a case where the illumination lens 26 has a large numerical aperture.

Figure 3:
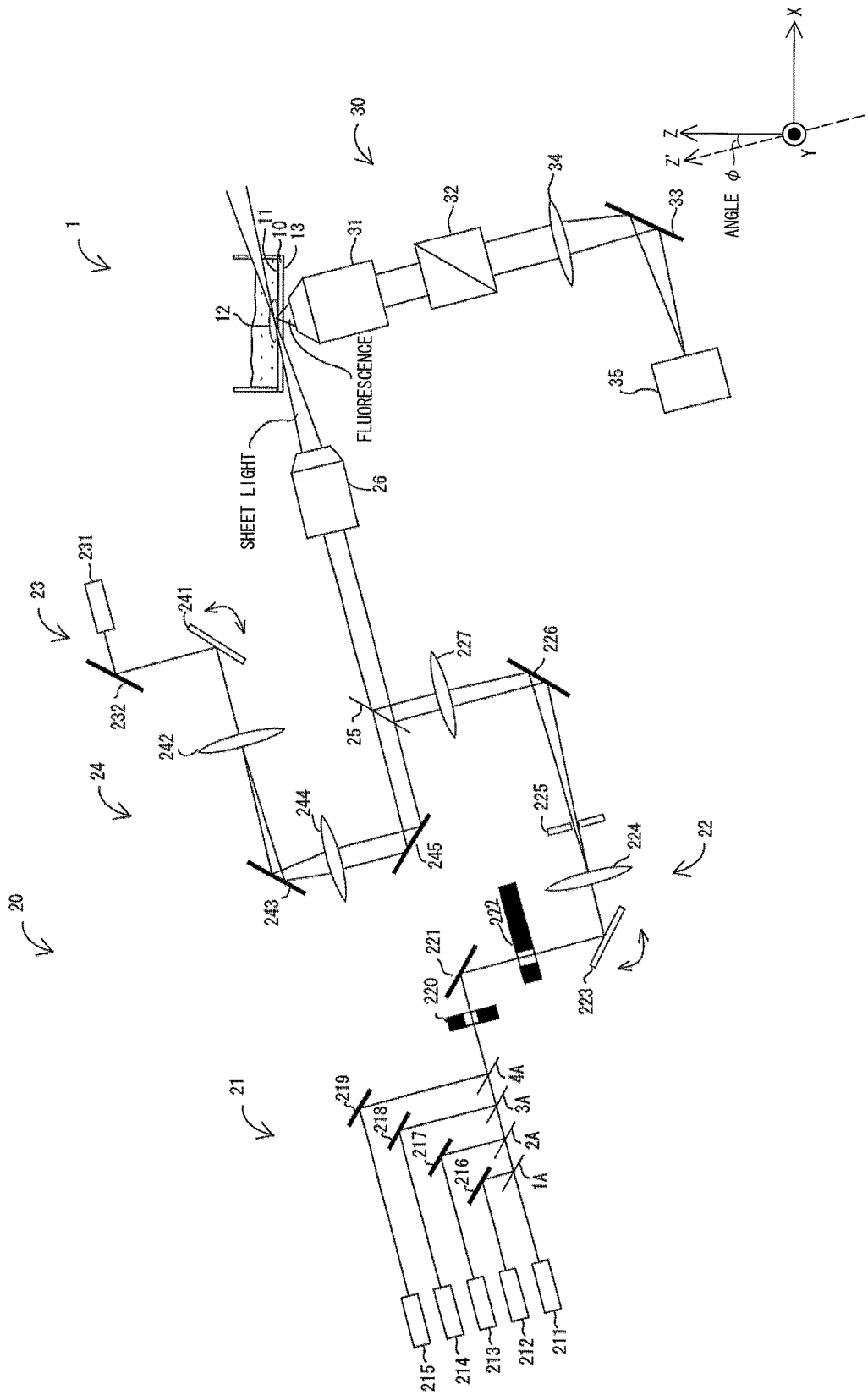
FIG. 3 is a diagram schematically illustrating an overall configuration and an optical path of a microscope of one embodiment of the present invention.

FIG. 3 is a diagram schematically illustrating an overall configuration and an optical path of the microscope 1 of the present embodiment. The microscope 1, as illustrated in FIG. 3, includes the optical unit 20 and an observation section 30 including the observation lens 31. The optical unit 20 generates sheet light, which irradiates a sample 12. The observation section 30 then receives fluorescence from the sample 12 at the observation lens 31 to form an image. The description below deals with arrangements of an optical unit and an observation section that are preferable for use in the overall configuration of the microscope 1 of the present embodiment and properties of sheet light for the case in which the microscope 1 includes such preferable optical unit and observation section.

<Optical Unit>The optical unit 20 includes a visible light source section 21, a visible light adjusting section 22, an IR light source section 23, an IR light adjusting section 24, a dichroic mirror (DM) 25, and an illumination lens 26 (illumination objective lens).

The visible light source section 21 includes a 592-nm laser light source 211, a 560-nm laser light source 212, a 514-nm laser light source 213, a 450-nm laser light source 214, a 405-nm laser light source 215, mirrors 216 to 219, and DMs 1A to 4A. The visible light source section 21 is arranged such that the laser light sources 211 to 215 emit laser beams having different wavelengths, and the laser beams are reflected by the reflecting surfaces of the mirrors 216 to 219 and/or the reflecting surfaces of the DMs 1A to 4A for reflecting light beams having the wavelengths, so that the optical paths of the laser beams having different wavelengths are aligned with one another. The visible light source section 21 thus emits a composed laser beam to the visible light adjusting section 22 via a shutter 220 and a mirror 221.

The visible light adjusting section 22 includes a filter foil 222, a one-dimensional scanning mirror 223, a lens 224, an iris 225, a mirror 226, and a lens 227. The visible light adjusting section 22 allows a laser beam from the visible light source section 21 to strike the one-dimensional scanning mirror 223 through the filter foil 222. The one-dimensional scanning mirror 223 is a mirror for scanning the laser beam one-dimensionally over its reflecting surface. The one-dimensional scanning mirror 223 is, for example, a MEMS mirror, a piezo mirror, or a galvano mirror. The reflecting surface of the one-dimensional scanning mirror 223 changes one-dimensionally on the basis of a sine function, so that the light reflected by the one-dimensional scanning mirror 223 is a light beam having an optical path with a fixed width. The visible light adjusting section 22 is arranged such that light beams are reflected by the one-dimensional scanning mirror 223 at its reflecting surface, focused by the lens 224, passed through the iris 225, reflected by the mirror 226 at its reflecting surface, converted by the lens 227 into parallel light having a width, and then emitted toward the DM 25. In a case where the visible light source section 21 includes a large number of laser light sources, an achromat lens can preferably be used for each of the lens 224 and the lens 227. Further, the one-dimensional scanning mirror 223 may be replaced with, for example, a cylindrical lens, an acousto-optic deflector, or a diffraction grating for adjustment of the width of sheet light. In other words, the optical unit 20 for the present invention includes a one-dimensional scanning mirror, a cylindrical lens, an acousto-optic deflector, a diffraction grating, or the like as a light distributing element.

The IR light source section 23 includes an IR laser light source section 231 and a mirror 232. The IR light source section 23 is arranged such that the IR laser light source section 231 emits an IR laser beam, and the mirror 232 reflects the IR laser beam at its reflecting surface, so that the IR laser beam is emitted toward the IR light adjusting section 24.

The IR light adjusting section 24 includes a one-dimensional scanning mirror 241, an IR lens 242, a mirror 243, an IR lens 244, and a mirror 245. The IR light adjusting section 24 is arranged such that the IR light source section 23 emits an IR laser beam, and the one-dimensional scanning mirror 241 reflects the IR laser beam at its reflecting surface, so that the IR laser beam will have an optical path with a fixed width. The IR light adjusting section 24 is further arranged such that the IR light beam as reflected by the one-dimensional scanning mirror 241 at its reflecting surface is focused by the IR lens 242, reflected by the mirror 243 at its reflecting surface, converted by the lens 244 into parallel light having a width, reflected by the mirror 245 at its reflecting surface, and then emitted toward the DM 25. The microscope 1 of the present embodiment may alternatively be arranged such that a sample radiates fluorescence through multiphoton excitation. In this case, an achromat lens can preferably be used for each of the IR lens 242 and the IR lens 244 as well. Since such multiphoton excitation requires a light source for an IR wave range and correction of chromatic aberration, the IR light source section 23 and the IR light adjusting section 24 each need to be designed independently of the visible light source section 21 and the visible light adjusting section 22.

The DM 25 is a dichroic mirror that reflects a visible light beam and passes an IR light beam through itself. The DM 25 passes, through one surface thereof, an IR light beam from the IR light adjusting section 24 and at the other surface, reflects a visible light beam from the visible light adjusting section 22 to align the optical paths of the IR light beam and the visible light beam with each other and then emit the IR light beam and the visible light beam toward the illumination lens 26.

The illumination lens 26 focuses the IR light beam and the visible light beam into sheet light and emits such sheet light toward a sample 12.

The individual optical elements included in the optical unit 20 such as light sources, lenses, and mirrors may be disposed on a surface of an optical surface plate. In this case, the optical surface plate is so oriented that the surface on which the optical elements are disposed is parallel to the observation plane. This arrangement allows generation of sheet light traveling in the direction parallel to the observation plane and simplifies the step of adjusting the configuration of the optical elements. The optical unit 20 of the present embodiment may be attached to a general upright microscope or inverted microscope for practice of the present invention.

The present embodiment has an example configuration in which an illumination lens 26 is disposed at the opening for emission of light from the optical unit 20. The optical unit 20 may, however, be configured without the illumination lens 26.

In the case where the illumination lens 26 is not used, adjusting the configuration of the lens 227 and the IR lens 244 in FIG. 3 can appropriately change the thickness of sheet light to be emitted by the optical unit 20. The lenses included in the optical unit 20 may each be replaced with a conical prism or diffraction grating as an optical element (light converging element) that focuses light similarly to a lens for generation of the sheet light.

<Observation Section>

The observation section 30 includes the observation lens 31 (detection objective lens), a fluorescence mirror cube 32, a mirror 33, an imaging lens 34, and a CCD camera 35. The observation lens 31 refracts light radiated from a sample 12 and emits the refracted light toward the fluorescence mirror cube (fluorescence filter) 32. The fluorescence mirror cube 32 passes, through itself, only the fluorescence from the sample 12 out of the light from the observation lens 31. The observation section 30 is arranged such that the imaging lens 34 collects fluorescence from the fluorescence mirror cube 32, and then the mirror 33 reflects the collected fluorescence at its reflecting surface, so that the reflected fluorescence enters the CCD camera 35. The observation section 30, through this operation, forms an image from fluorescence radiated from the sample 12.

<Properties of Sheet Light>

The description below deals with sheet light of the microscope 1 of the present embodiment. Fluorescence radiated from that portion of a sample which is not the observation plane composes the background for the observation plane of the observation lens 31. To reduce the background, the illuminated region preferably has a small thickness. The microscope 1 of the present embodiment forms an illuminated region having a thickness D of 3 µm or less.

Figure 4:
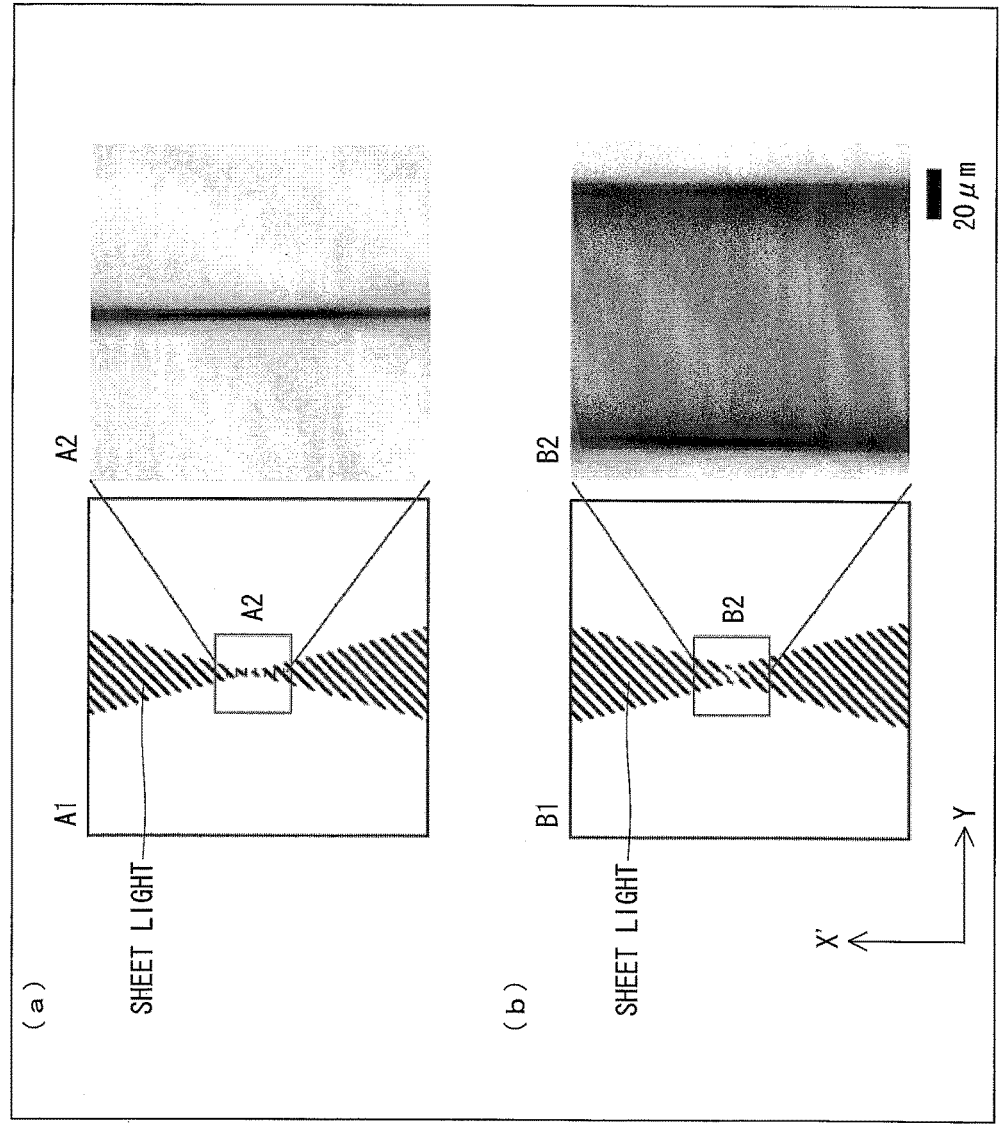
FIG. 4 illustrates shapes of sheet light of a microscope of one embodiment of the present invention.

FIG. 4 illustrates shapes of sheet light of the microscope 1 of the present embodiment. (a) of FIG. 4 shows a diagram (A1) schematically illustrating an optical path of sheet light and a fluorescence image (A2) formed by the observation section 30 for a case in which scanning by the one-dimensional scanning mirror is off. (b) of FIG. 4 shows a diagram (B1) schematically illustrating an optical path of sheet light and a fluorescence image (B2) formed by the observation section 30 for a case in which scanning by the one-dimensional scanning mirror is on. The X' direction in FIG. 4 indicates the direction of the optical axis of the illumination lens, and the Y direction in FIG. 4 is identical to that of FIGS. 1 through 3. The fluorescence images of FIG. 4 are fluorescence images that have been produced by irradiating, with laser light (592 nm), an aqueous solution containing fluorescence molecules (rhodamine) which aqueous solution is sandwiched between the sample placement part 10 and a slide glass and with use of the CCD camera 35, capturing an image of fluorescence radiated from the sample. Also by adjusting the scan width of the one-dimensional scanning mirror 233, it is possible to control the width W of a region illuminated with sheet light. FIG. 4 illustrates a fluorescence image for a case in which the one-dimensional scanning mirror 233 has scanned light beams one-dimensionally so that the region illuminated with sheet light has a width W of 100 µm along the Y direction. Further, also by controlling the iris 225 to open or close it, the width W of the region illuminated with sheet light can be controlled. In addition, the illumination lens may be provided with an aperture stop attached thereto so that controlling the aperture stop can adjust the thickness D and light collection depth of the region illuminated with sheet light. Reducing the opening of the aperture stop increases the thickness D and light collection depth of sheet light.

Figure 5:
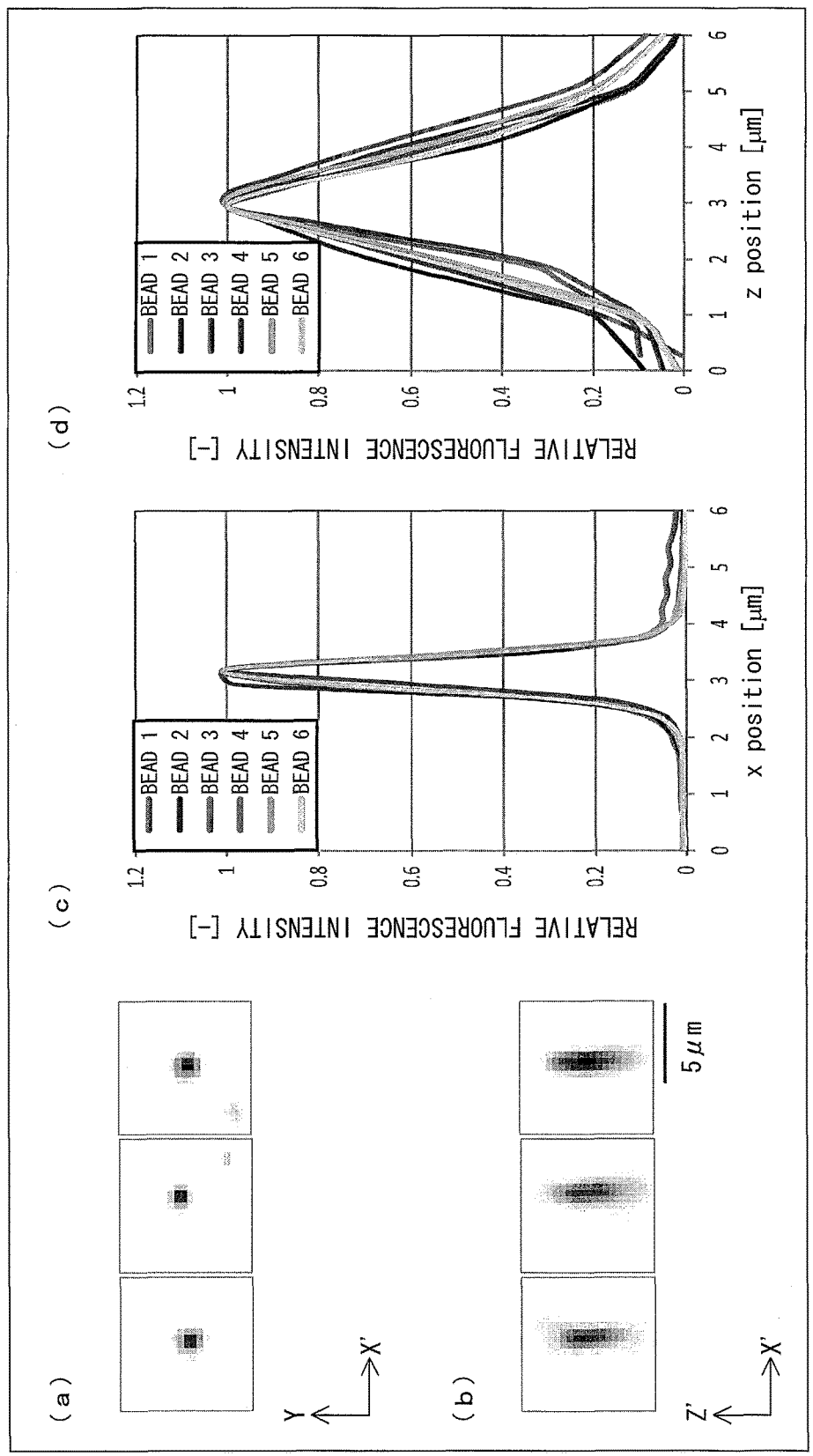
FIG. 5 illustrates images of a sample that are produced with use of a microscope of one embodiment of the present invention and fluorescence intensity distributions of the sample.

FIG. 5 illustrates properties of sheet light of the microscope 1 of the present embodiment. The X' direction in FIG. 5 is identical to that of FIG. 4, and the Z' direction in FIG. 5 is identical to those of FIGS. 1 through 3. (a) of FIG. 5 shows images of a sample on the X'-Y plane that are produced by scanning the sample placement part with respect to sheet light. (b) of FIG. 5 shows images of a sample on the X'-Z' plane that are produced as above. The images of (a) and (b) of FIG. 5 are fluorescence images produced by scanning the sample placement part 10 along the Z' direction in steps of 1 µm for minute fluorescence beads (D=0.04 µm) fixed in 1 weight % of agarose gel and with use of the CCD camera 35, capturing an image of fluorescence radiated from the sample.

(c) of FIG. 5 is a graph indicative of a distribution of fluorescence intensity of the images along the X' direction. (d) of FIG. 5 is a graph indicative of a distribution of fluorescence intensity of the images along the Z' direction. An analysis of the fluorescence intensity distributions in (c) and (d) of FIG. 5 shows that the fluorescence intensity along the X direction has a half-value width of 0.87 µm and that the fluorescence intensity along the Z direction has a half-value width of 2.6 µm. The results of the analysis prove that the region illuminated with sheet light by the microscope 1 has a width of 2.6 µm along the Z direction.

[Comparative Examples]

Figure 6:
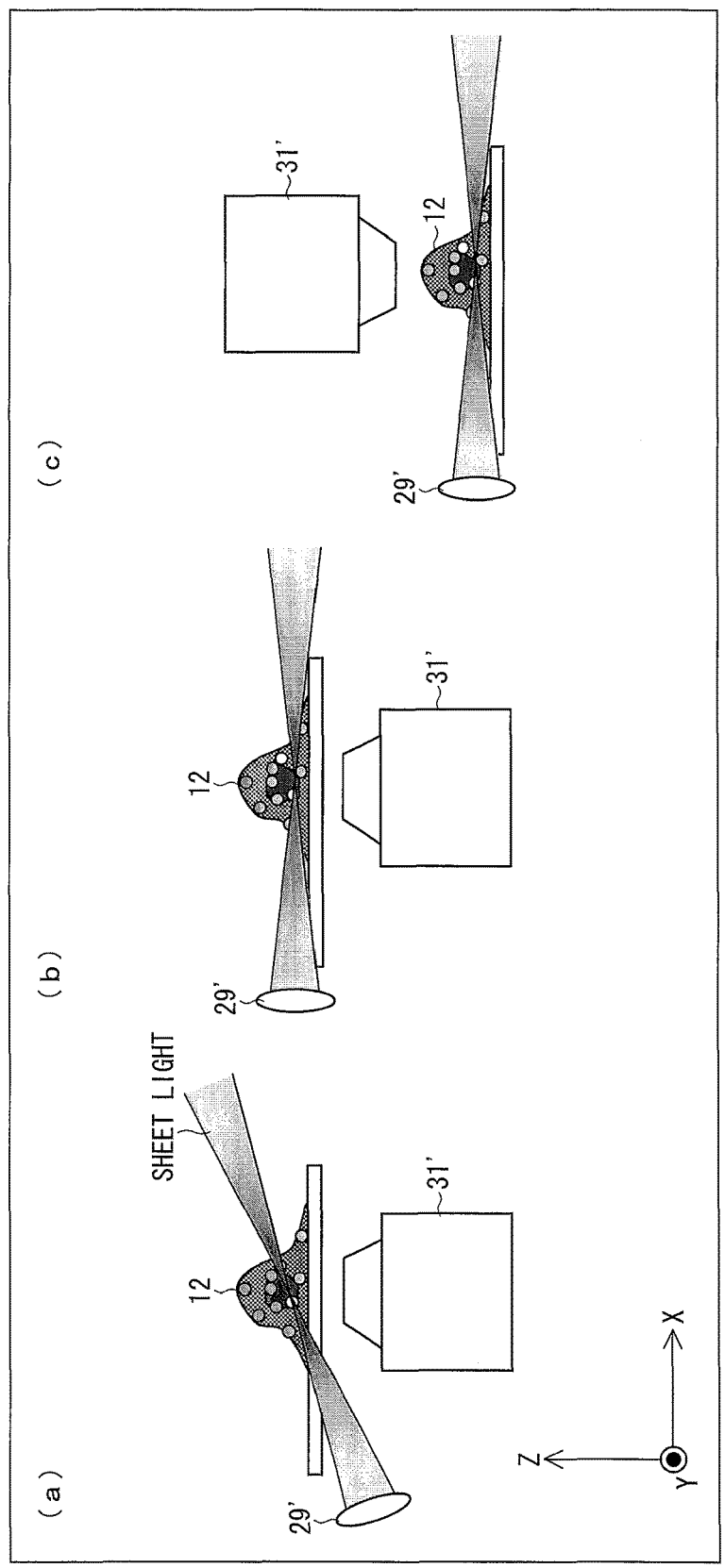
FIG. 6 shows diagrams each schematically illustrating a configuration of a microscope of a comparative example.

FIG. 6 shows diagrams each schematically illustrating a configuration of a microscope as a comparative example. (a) of FIG. 6 illustrates a configuration of a microscope as a first comparative example. (b) of FIG. 6 illustrates a configuration of a microscope as a second comparative example. (c) of FIG. 6 illustrates a configuration of a microscope as a third comparative example.

The microscope illustrated in (a) of FIG. 6 as the first comparative example is arranged such that the observation lens 31' has an optical axis that is not orthogonal to the optical axis of the illumination lens 26' and that is not parallel to the thickness direction of an illuminated region in a plane perpendicular to the optical axis of the illumination lens 26'. This arrangement results in an image being ununiformly out of focus to varying degrees over the observation plane, the image thus having decreased quality evenness. Further, the above arrangement lets sheet light irradiate that portion of a sample which is not the observation plane, with the result of a large background.

The microscope illustrated in (b) of FIG. 6 as the second comparative example is arranged such that the observation lens 31' has an optical axis that is orthogonal to the optical axis of the illumination lens 26' and that is parallel to the thickness direction of an illuminated region in a plane perpendicular to the optical axis of the illumination lens 26'. The illumination lens 26' is, however, disposed on the same side as a sample with respect to a plane including the placement surface.

The microscope illustrated in (c) of FIG. 6 as the third comparative example is arranged such that the observation lens 31' has an optical axis that is orthogonal to the optical axis of the illumination lens 26' and that is parallel to the thickness direction of an illuminated region in a plane perpendicular to the optical axis of the illumination lens 26'. The illumination lens 26' and the observation lens 31' are, however, disposed on the same side as a sample with respect to a plane including the placement surface.

The microscope as the second comparative example and the microscope as the third comparative example are both arranged such that the illumination lens is disposed on the same side as a sample with respect to the plane including the placement surface. Since increasing the numerical aperture of the illumination lens widens the optical path of sheet light along the Z direction, the microscope as the second comparative example and the microscope as the third comparative example will both let part of sheet light be separated by the sample placement part before illuminating an observation plane. The resulting sheet light will have a large thickness and thus illuminate a region of a sample which region is other than the observation plane, with the result of a large background. In particular, in a case of observing a sample in the vicinity of the placement surface, the illumination lens needs to have an optical axis close to the plane including the placement surface so that the sample will have an illuminated region close to the placement surface. In a case where the illumination lens has an optical axis close to the placement surface, sheet light is more likely separated by the placement surface before illuminating the observation plane. The microscopes as the second comparative example and the third comparative example are, as described above, incapable of observing a sample at a high resolution by increasing the numerical aperture of the illumination lens. In particular, the microscopes as the second comparative example and the third comparative example fail to allow observation of a sample at a high resolution in the vicinity of the placement surface.

[Further Embodiment]

The description below deals with another embodiment of the present invention with reference to FIGS. 7 through 10. For convenience of explanation, any member of the present embodiment that is identical in function to a corresponding member described for Embodiment 1 is assigned an identical reference numeral, and is not described here.

<Focusing Mechanism>

Figure 7:
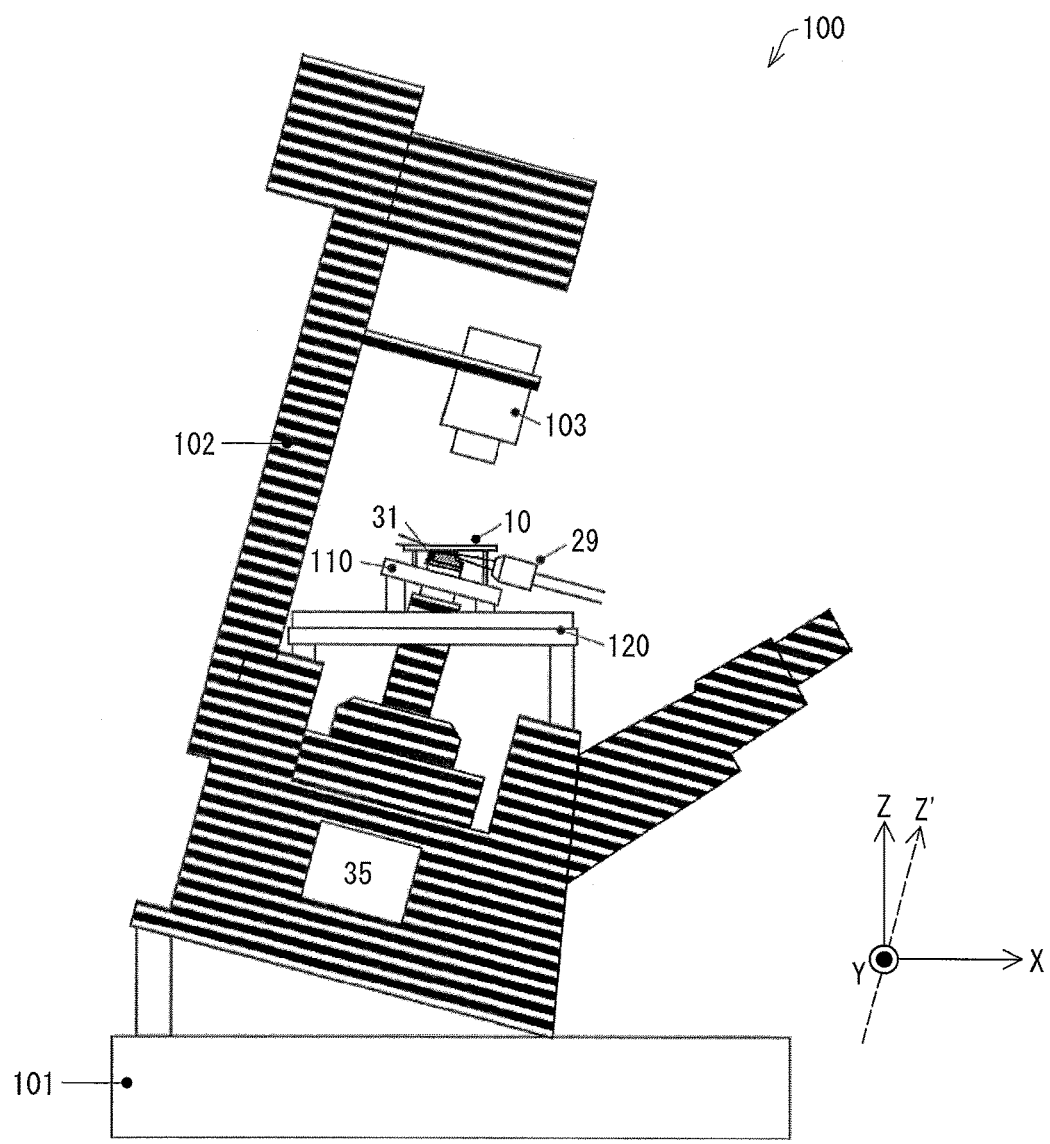
FIG. 7 is a diagram schematically illustrating a configuration of a microscope of one embodiment of the present invention.

FIG. 7 is a diagram schematically illustrating a configuration of a microscope 100 of the present embodiment.

The microscope 100, as illustrated in FIG. 7, includes a vibration removal table 101, a microscope body 102 on the vibration removal table 101, and a condenser 103 for irradiating a sample 12 from above.

The microscope 100 further includes a first stage 110 and a second stage 120 together as a focusing mechanism for adjusting the relative positional relationship between a sample placement part 10 and an observation lens 31. The first stage 110 is placed on the second stage 120. The first stage 110 includes a jig for fixing the sample placement part 10, and the sample placement part 10 is fixed to the first stage 110 by means of the jig.

The first stage 110 is capable of changing the position of the sample placement part 10 relative to the observation lens 31 along a first direction (that is, the Z' direction in FIG. 7), which is identical to the direction of the optical axis of the observation lens 31. The second stage 120 is capable of changing the position of the sample placement part 10 relative to the observation lens 31 along a second direction and third direction (that is, the X direction and Y direction in FIG. 7) that define a placement surface of the sample placement part 10.

The microscope 100, as described above, allows adjustment of the relative positional relationship between the observation lens 31 and the sample placement part 10 along each of the first to third directions. The relative positional relationship between the observation lens 31 and the sample placement part 10 may alternatively be adjusted by fixing the position of the sample placement part 10, placing the observation lens 31 and the illumination lens 26 respectively on the first stage 110 and the second stage 120, and changing the positions of the observation lens 31 and the illumination lens 26.

FIG. 7 illustrates an embodiment in which the first stage with a jig attached thereto is placed on the second stage. The first stage and the second stage can function as a focusing mechanism suitable for the present invention also in a case where a jig is attached to the second stage as long as that second stage is placed on the first stage.

Figure 8:
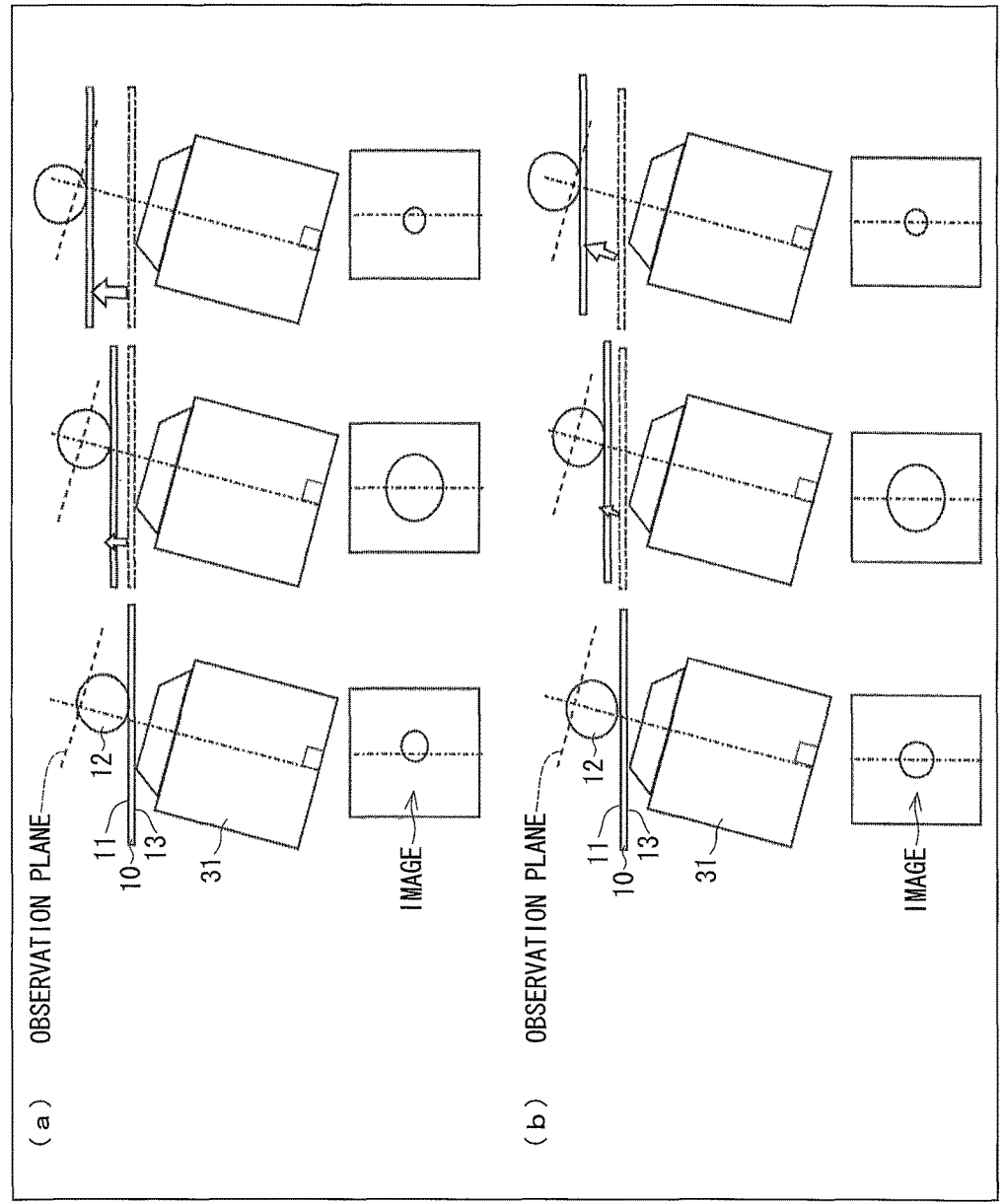
FIG. 8 shows diagrams each illustrating how an image changes in response to a change in the positional relationship between an observation lens and sample placement part of a microscope of one embodiment of the present invention.

FIG. 8 shows diagrams each illustrating how the position of an image changes within an identical field of view in response to a change in the positional relationship between an observation lens and a sample placement part. (a) of FIG. 8 illustrates how the position of an image changes within an identical field of view in response to a change in the position of a sample placement part relative to an observation lens along a direction perpendicular to a placement surface (that is, the Z direction in FIG. 7). (b) of FIG. 8 illustrates how the position of an image changes within an identical field of view for the microscope of the present embodiment in response to a change in the position of the sample placement part relative to the observation lens along the direction of the optical axis of the observation lens (that is, the Z' direction in FIG. 7).

In a case where the position of a sample placement part is changed along the direction perpendicular to a placement surface as illustrated in (a) of FIG. 8, the position of an image undesirably changes within a field of view of an observation lens. In contrast, the microscope 100, which has the focusing mechanism described above, is arranged such that changing the position of the sample placement part along the first direction (that is, the direction of the optical axis of the observation lens 31) as illustrated in (b) of FIG. 8 can achieve focus without changing the position of an image within a field of view observed. This arrangement makes it possible to continuously capture an image of a sample for formation of a three-dimensional image with the image fixed within an identical field of view.

The microscope 100, which has the focusing mechanism described above, is arranged such that adjusting the relative positional relationship between the observation lens 31 and the sample placement part 10 along the second direction and third direction can change an observed field of view without changing the distance between the sample placement part 10 and the observation lens 31. This arrangement can prevent unnecessary contact between the sample placement part 10 and the observation lens 31 while the microscope 100 changes the observed field of view.

The focusing mechanism as part of the microscope 100 may alternatively be a separate focusing device for use in a conventionally publicly known microscope.

<Fluid Holding Device>

Figure 9:
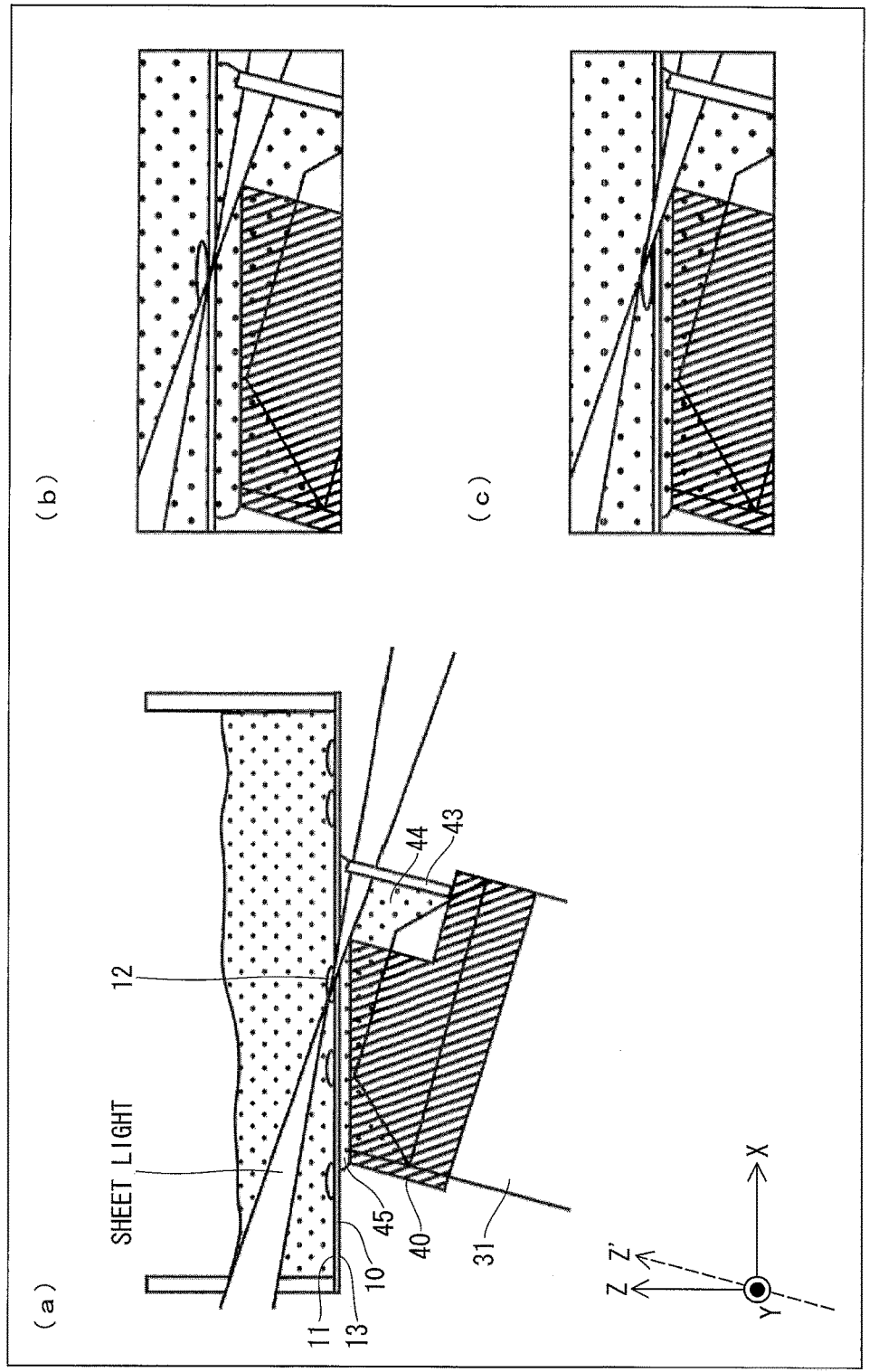
FIG. 9 shows diagrams each schematically illustrating a main configuration of a microscope of one embodiment of the present invention.

FIG. 9 shows diagrams each schematically illustrating a main configuration of the microscope 100. (a) of FIG. 9 is a diagram schematically illustrating a sample placement part and an observation lens with a fluid holding device connected thereto. (b) of FIG. 9 is a diagram schematically illustrating a sample placement part and an observation lens for a case where the sample placement part is separated from the observation lens. (c) of FIG. 9 is a diagram schematically illustrating a sample placement part and an observation lens for a case where a sample is close to the observation lens.

Figure 10:
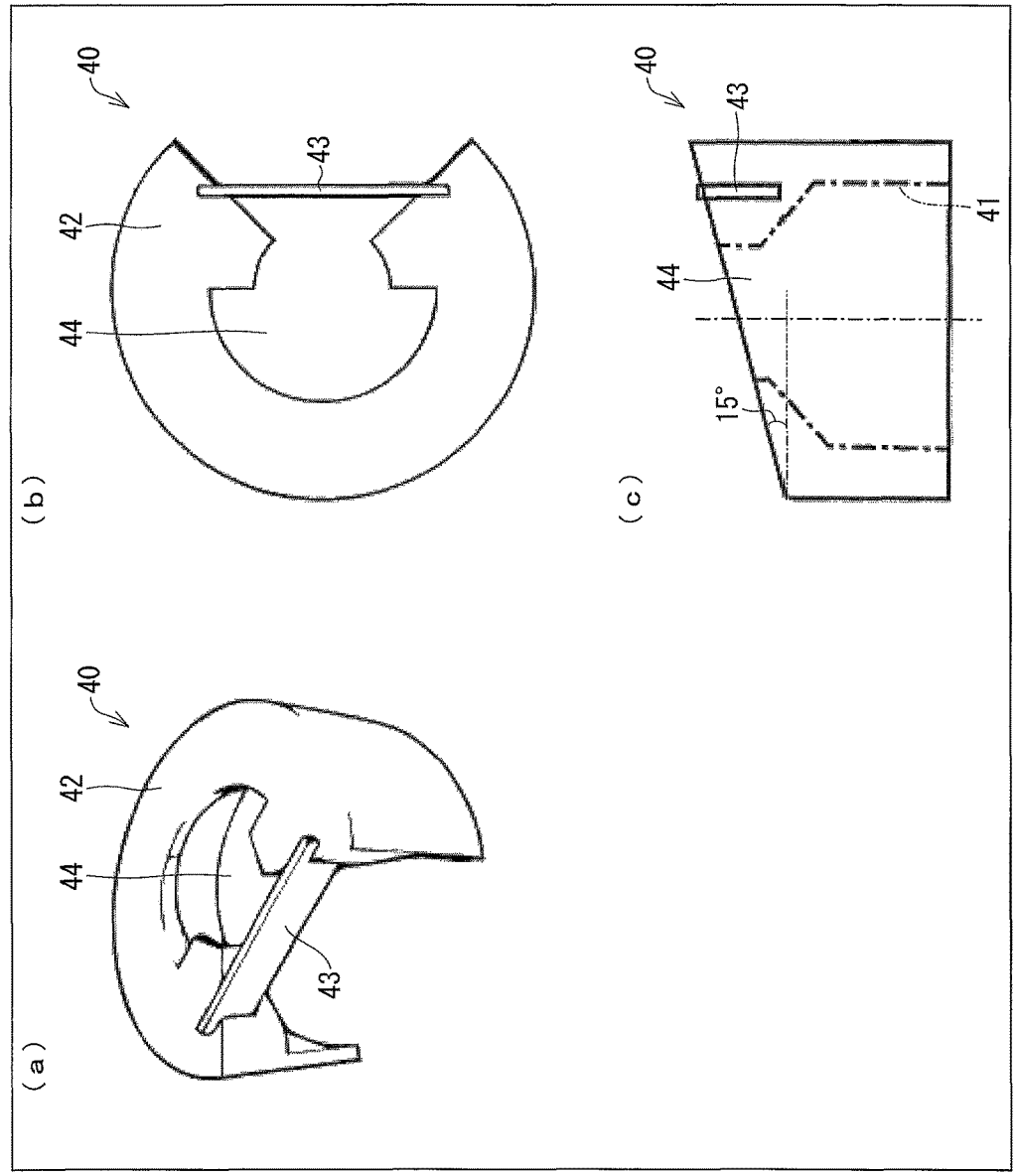
FIG. 10 shows diagrams each schematically illustrating a main configuration of a microscope of one embodiment of the present invention.

The microscope 100, as illustrated in (a) of FIG. 9, includes a fluid holding device 40 between the observation lens 31 and the sample placement part 10. FIG. 10 shows diagrams each schematically illustrating the fluid holding device. (a) of FIG. 10 is a perspective view of the fluid holding device. (b) of FIG. 10 is a top view of the fluid holding device as connected to an observation lens, the view being taken along the optical axis of the observation lens. (c) of FIG. 10 is a cross-sectional view of the fluid holding device as connected to the microscope 100 via an observation lens, the view being taken on a plane defined by the optical axis of an illumination lens and the optical axis of the observation lens.

The shape of the fluid holding device 40 is, as illustrated in FIG. 10, a substantially cylindrical shape to fit with the observation lens 31 to be connected, and its inside has a hollowed structure. The fluid holding device 40 includes a connection section 41 for connection to the observation lens 31, an end face 42 at such a position as to face the bottom face 13 of the sample placement part 10 so that the sample placement part 10 is placed on the end face 42, and a transmission window 43 that allows light to pass therethrough. In a state where the fluid holding device 40 is connected to the observation lens 31, the hollow forms a fluid holding section 44 for holding fluid inside itself.

FIG. 9 illustrates an embodiment in which the fluid holding section 44 is filled with water 45, and the observation lens 31 is a water-immersion lens. The fluid holding section 44 may be filled with a fluid corresponding to the lens to be used; for example, in a case where the observation lens 31 is an oil-immersion lens, the fluid holding section 44 may be filled with an immersion oil. In a case where the observation lens 31 is a dry lens, the fluid holding device 40 may be used, or need not be used.

When the microscope 100 is in a state where the fluid holding device 40 and the sample placement part 10 are so positioned that the end face 42 faces the bottom face 13, the fluid holding device 40 may hold fluid in the fluid holding section 44 together with the bottom face 13. In this state, the end face 42 is substantially parallel to the bottom face 13 of the sample placement part 10. A portion of the water 45 is held between the end face 42 and the bottom face 13 as illustrated in FIG. 9 due to the surface tension of the water 45 filling the fluid holding section 44.

In a case where the microscope 100 is in a state where the fluid holding device 40 is connected to the observation lens 31, the illumination lens 26 disposed outside the fluid holding device 40 may irradiate a sample 12 with sheet light through the transmission window 43 and the fluid holding section 44. Specifically, the fluid holding device 40 includes a fluid holding section 44 that is a hollow extending from the transmission window 43 to the end face 42 such that sheet light from the illumination lens 26 which sheet light has passed through the transmission window 43 irradiates the sample 12. Further, the fluid holding device 40 includes a fluid holding section 44 that is a hollow extending, in the state where the fluid holding device 40 is connected to the observation lens 31, from the end face 42 to the connection section 41 such that fluorescence from the sample 12 is received by the observation lens 31. As described above, the microscope 100, which includes the fluid holding device described above, is capable of holding fluid such as liquid or gas between the observation lens 31 and the sample placement part 10 while ensuring a path of sheet light and a path of fluorescence. Further, by filling the fluid holding section 44 with liquid, the shape of the surface of the liquid does not change when, for example, the sample 12 is moved, and the surface of the liquid has a stable shape in correspondence with the shape of the fluid holding section 44. As described above, in the case where the microscope 100 includes an immersion lens as the observation lens 31, the microscope 100, which includes the fluid holding device described above, can irradiate a sample 12 with sheet light through a liquid having a stable surface shape, and can thus form an illuminated region at a desired position.

The fluid holding device as part of the microscope 100 may alternatively be a separate fluid holding device for use in a conventionally publicly known microscope.

<Sample Placement Part>

Figure 11:
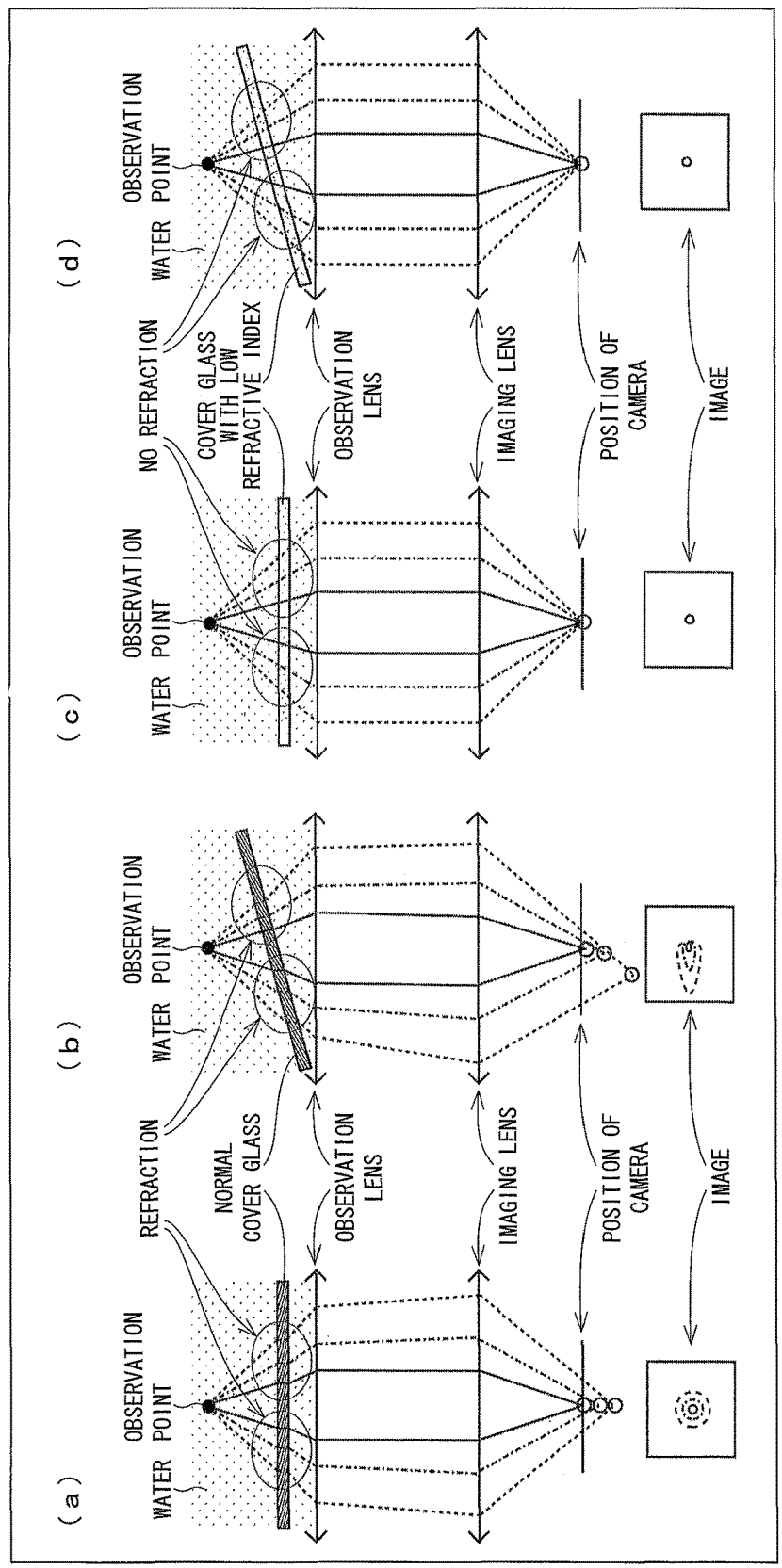
FIG. 11 shows diagrams illustrating aberration correction by a microscope of one embodiment of the present invention.

FIG. 11 shows diagrams each schematically illustrating a main configuration of the microscope 100. The diagrams each illustrate an optical path of fluorescence from a sample, the angle between a sample placement part and the optical axis of an observation lens, and an image formed by an observation section.

In a case where the observation lens is an immersion lens, the space between the sample placement part and the observation lens is filled with a desired liquid. In this case, the difference between the refractive index of the sample placement part and that of the above-mentioned liquid causes the optical path of fluorescence from a sample to change by refraction. Thus, even though the sample placement part has an observation plane perpendicular to the optical axis of the observation lens, aberration will emerge depending on the numerical aperture of the observation lens, with the result of unstable imaging (see (a) of FIG. 11). Such aberration may be removed with use of a correction collar for the observation lens. However, in a case where the sample placement part has an observation plane not perpendicular to the optical axis of the observation lens (that is, the sample placement part is inclined from a plane perpendicular to the optical axis of the observation lens), left-right asymmetric aberration will emerge which is extremely difficult to remove (see (b) of FIG. 11).

The microscope 100 is, in the case where the observation lens is a water-immersion lens, preferably arranged such that the sample placement part is made of a material having a refractive index equivalent to that of water (1.28 to 1.38) which material is typified by an amorphous fluorine resin having the following structural formula:

[Chem. 1]

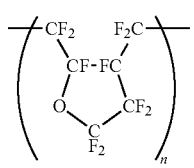

The above arrangement can prevent light refraction at the sample placement part and can thus significantly reduce aberration that occurs depending on the numerical aperture of the observation lens, thereby allowing the microscope to form a stable image (see (c) of FIG. 11). Further, even though the sample placement part has an observation plane not perpendicular to the optical axis of the observation lens, the above arrangement can prevent the emergence of left-right asymmetric aberration (see (d) of FIG. 11). The above resin is commercially available as CYTOP (registered trademark). The sample placement part of the microscope 100 may alternatively be made of another fluorine-based transparent resin. Further, Lumox may alternatively be used as the sample placement part. In this case, even though the sample placement part is to be made of a material having a refractive index different from that of water, reducing the thickness of the sample placement part can reduce effect of refraction.

Specific preferable examples of the sample placement part are described above. The sample placement part is, however, not limited to those. The sample placement part may suitably be any planar substrate that is thin and transparent and that has a refractive index (1.28 to 1.38) equivalent to that of water. The sample placement part 10, which is in the shape of a planar substrate, requires both strength to hold a sample and thinness sufficient to prevent influence on observation. The thickness is preferably within the range from 1 μm to 200 μm. In particular, in a case of observing a sample on a sample placement part 10 as Lumox (®), with a refractive index of 1.36), the sample placement part 10 preferably has a thickness within the range from 10 μm to 50 μm to reduce aberration caused by the sample placement part 10 and to allow stable observation. In a case of observe a sample on a sample placement part 10 made of CYTOP (®), with a refractive index of 1.34), the sample placement part 10 preferably has a thickness within the range from 10 μm to 100 μm to reduce aberration caused by the sample placement part 10 and to allow stable observation.

<Further Arrangement>

The description below deals with other features of the microscopes 1 and 100 of the present invention.

(Visible Light Adjusting Section)

Figure 12:
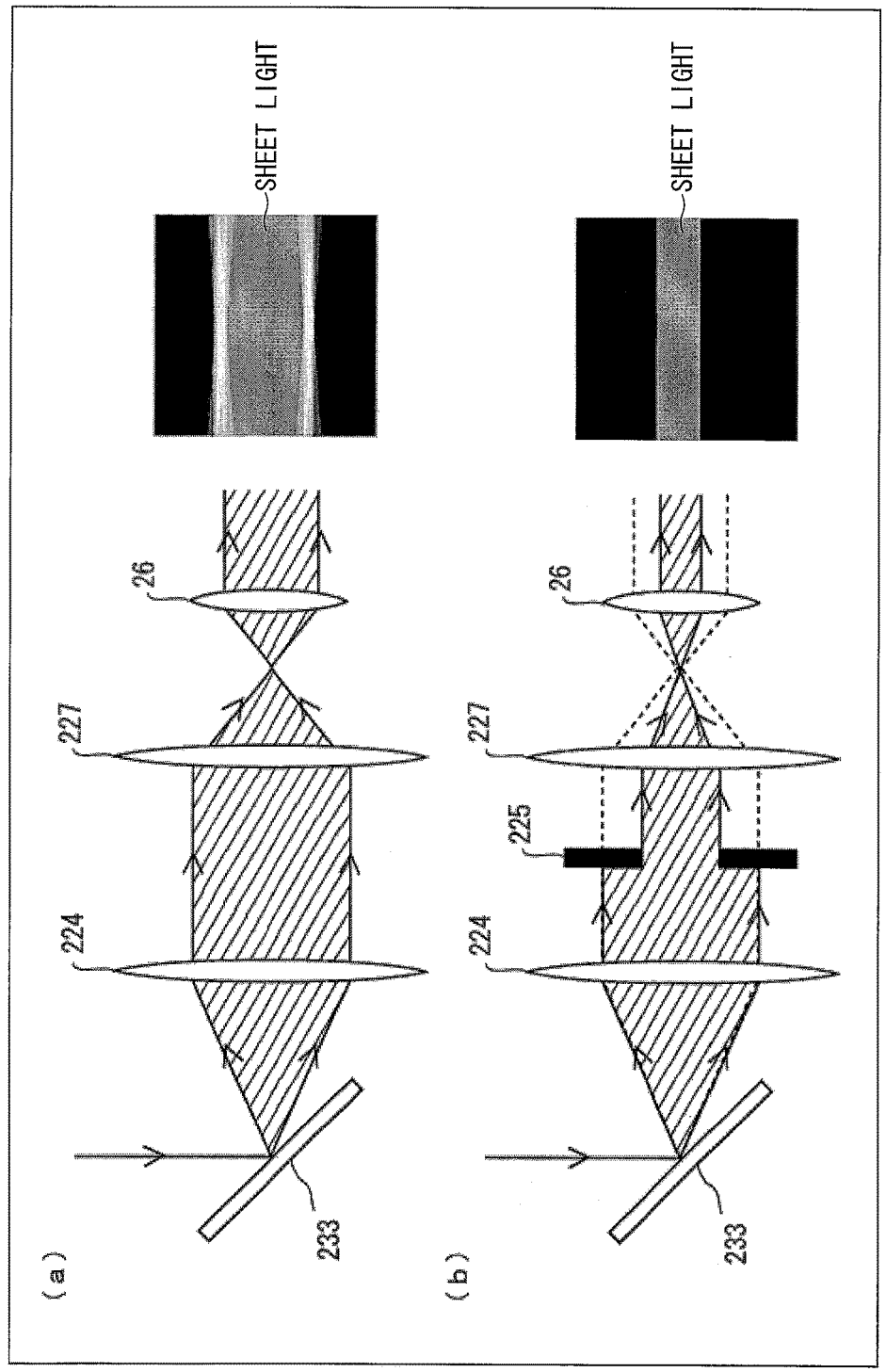
FIG. 12 shows diagrams each illustrating an optical path and a luminance distribution of a light beam in an optical unit.
Figure 13:
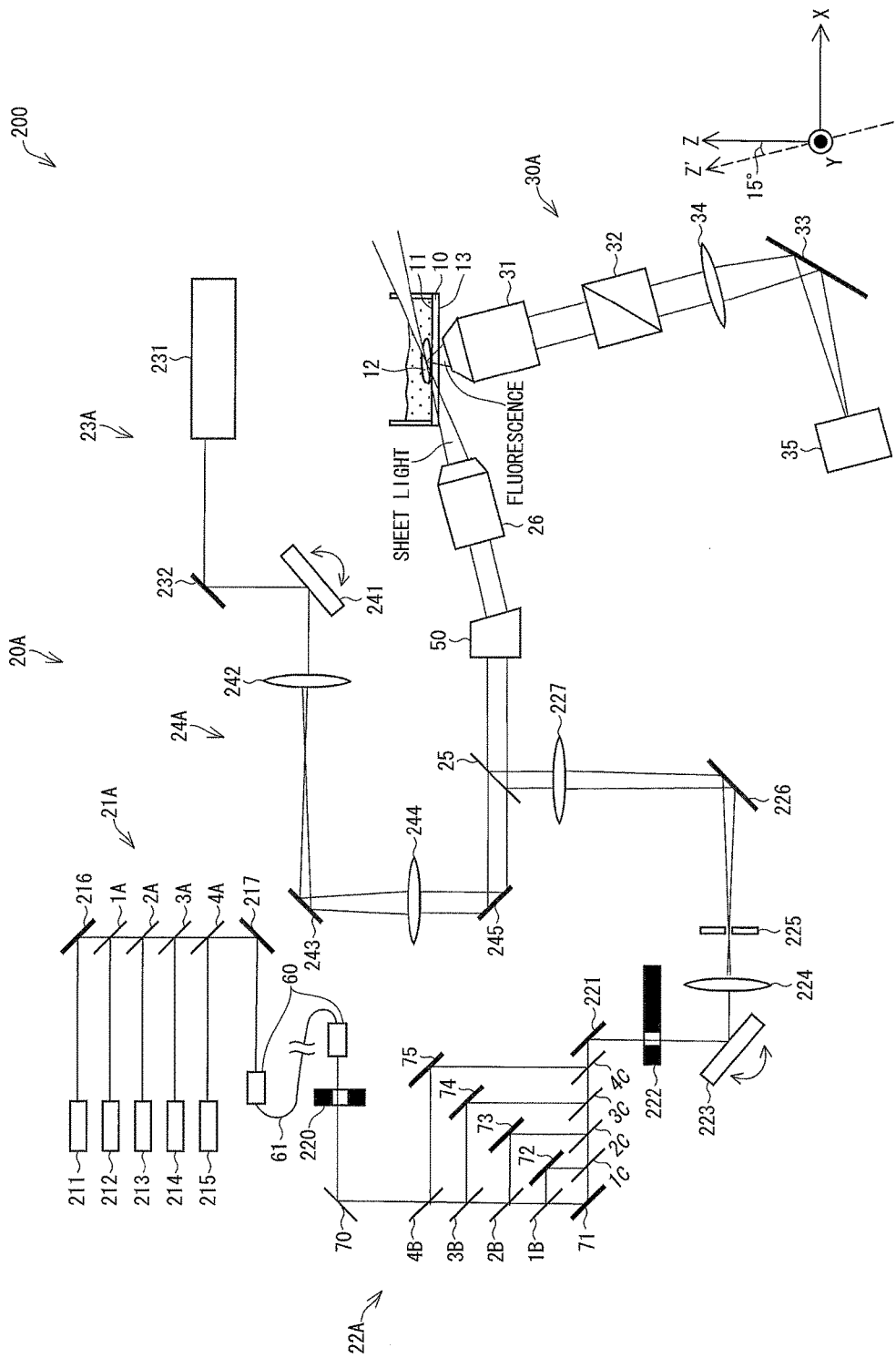
FIG. 13 is a diagram schematically illustrating an overall configuration and an optical path of a microscope of a variation of the present invention.

The microscopes 1 and 100 of the present invention are both arranged such that the one-dimensional scanning mirror 233 reflects, at its reflecting surface, light from the laser light sources 211 to 215 to uniformly distribute light in the Y-axis direction shown in FIGS. 12 and 13.

FIG. 12 shows diagrams each illustrating an optical path and a luminance distribution of a light beam in the optical unit. (a) of FIG. 12 illustrates a light beam reflected at the reflecting surface of a one-dimensional scanning mirror and a light luminance distribution. (b) of FIG. 12 illustrates a light beam reflected at the reflecting surface of a one-dimensional scanning mirror and passing through an iris and a light luminance distribution. The one-dimensional scanning mirror 233 scans its reflecting surface one-dimensionally on the basis of a sine function. Thus, as illustrated in (a) of FIG. 12, light reflected by the one-dimensional scanning mirror 233 has higher luminance at edges in the width direction than in the middle of the light beam. The microscopes 1 and 100 of the present embodiment are, in view of that, both arranged to produce light with uniform luminance as illustrated in (b) of FIG. 12 by reflecting light at the one-dimensional scanning mirror 233, collecting the light at the lens 224, and then passing the light through the iris 225 to remove edges of the light beam in the width direction.

<Variations>

The description below deals with variations of the present invention with reference to FIGS. 13 through 15. For convenience of explanation, any member of the present embodiment that is identical in function to a corresponding member described for Embodiment 1 is assigned an identical reference numeral, and is not described here.

FIG. 13 is a diagram schematically illustrating an overall configuration and an optical path of a microscope 200 of a variation of the present invention. The microscope 200, as illustrated in FIG. 13, includes a sample placement part 10, an optical unit 20A, and an observation section 30A.

The optical unit 20A includes a visible light source section 21A, a visible light adjusting section 22A, an IR light source section 23A, an IR light adjusting section 24A, a dichroic mirror (DM) 25, an illumination lens 26 (illumination objective lens), and a wedge prism 50.

The visible light source section 21A is arranged such that the laser light sources 211 to 215 emit laser beams having different wavelengths and that the laser beams are reflected by the reflecting surface of a mirror 216 and/or the reflecting surfaces of DMs 1A to 4A for reflecting light beams having the wavelengths, so that the optical paths of the laser beams having different wavelengths are aligned with one another. The visible light source section 21A is arranged such that the laser beams having the wavelengths and optical paths aligned with one another are reflected at the reflecting surface of a mirror 217 and are then composed with use of fiber coupler 60s and a fiber 61. The visible light source section 21A thus emits a composed laser beam to the visible light adjusting section 22A via a shutter 220.

The visible light adjusting section 22A includes mirrors 70 to 75, a mirror 221, DMs 1B to 4B, DMs 1C to 4C, a filter foil 222, a one-dimensional scanning mirror 223, a lens 224, an iris 225, a mirror 226, and a lens 227. The visible light adjusting section 22A is arranged to reflect laser beams from the visible light source section 21A at the reflecting surface of the mirror 70 and then reflect the laser beams at the reflecting surfaces of the DMs 1B to 4B, mirrors 71 to 75, and DMs 1C to 4C at different reflection angles corresponding to the wavelengths so as to separate, from one another, the optical paths of the laser beams having the different wavelengths. The visible light adjusting section 22 A allows the laser beams to strike the one-dimensional scanning mirror 223 through the filter foil 222, and thus allows parallel light having a fixed width to be emitted toward the DM 25.

The IR light source section 23A and IR light adjusting section 24A are the same respectively as the IR light source section 23 and IR light adjusting section 24 of Embodiment 1. The IR light adjusting section 24A emits an IR light beam toward the DM 25.

The DM 25 passes an IR light beam from the IR light adjusting section 24A through one surface thereof and at the other surface, reflects a visible light beam from the visible light adjusting section 22 A to align the optical paths of the IR light beam and the visible light beam with each other and to then emit the IR light beam and the visible light beam toward the wedge prism 50. The wedge prism 50 bends the IR light beam and the visible light beam and then emits the IR light beam and the visible light beam toward the illumination lens 26.

The microscope 1 of Embodiment 1 is, in order to irradiate a sample 12 with sheet light through the bottom face 13 of the sample placement part 10, arranged such that as illustrated in FIG. 3, the illumination lens 26 has an optical axis inclined at the angle ϕ with respect to the placement surface 11, and the other members of the optical unit 20 are also disposed at the angle ϕ. Assuming that the Z direction in FIG. 3 is the vertical direction, it will not be easy to dispose the individual members of the optical unit 20 with reference to the Z' direction, which is inclined at the angle ϕ from the Z direction.

In view of that, as the microscope 200 of the variation, the microscope 1 of Embodiment 1 may be equipped with a wedge prism 50 provided between the DM 25 and the illumination lens 26 to bend light beams between the DM 25 and the illumination lens 26. This arrangement eliminates the need to adjust the orientations of the individual members of the optical unit 20 in correspondence with the angle ϕ, thereby facilitating assembly of the optical unit 20.

Figure 14:
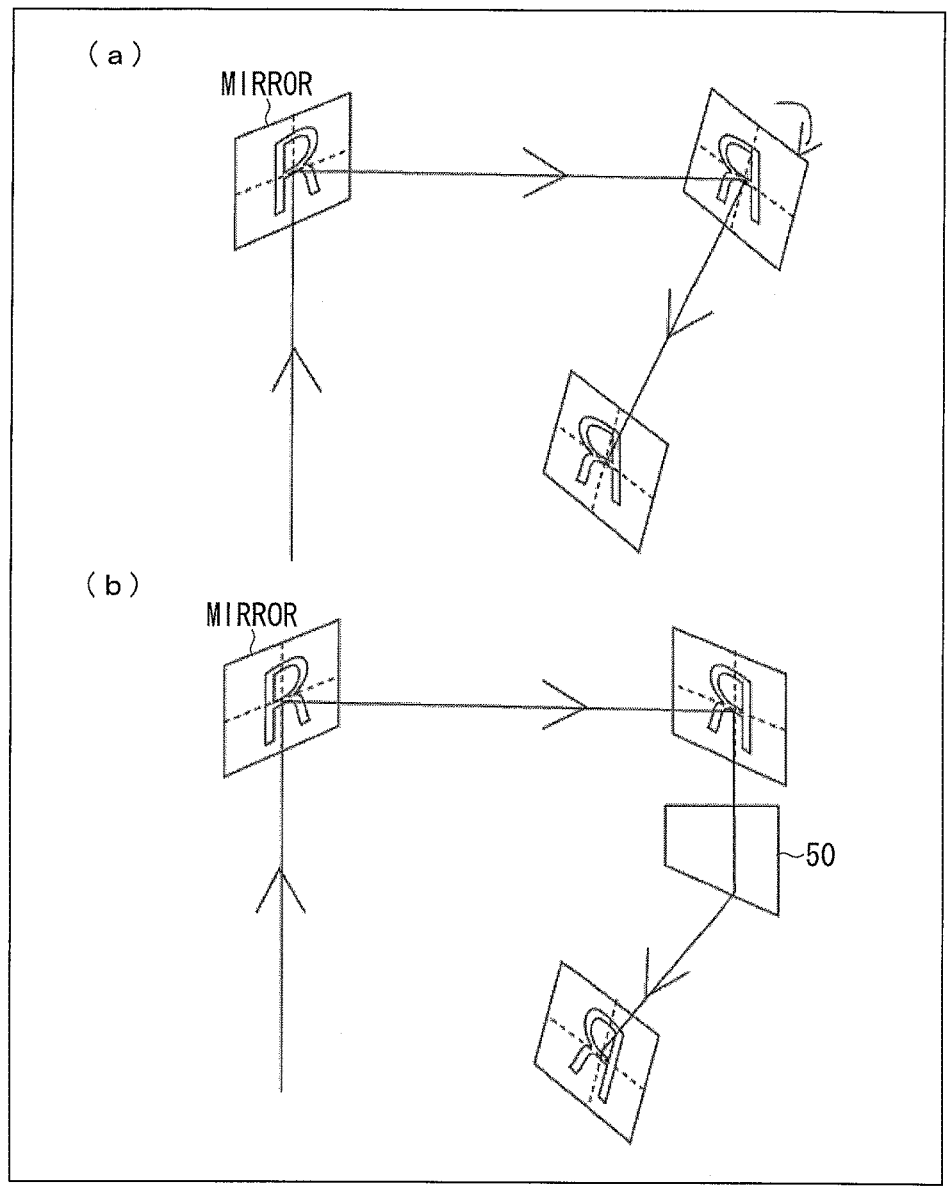
FIG. 14 shows diagrams each illustrating an arrangement for bending a light beam in an optical unit.

FIG. 14 illustrates arrangements each for bending a light beam. (a) of FIG. 14 illustrates an arrangement for bending a light beam by reflecting the light beam at the reflecting surface of a mirror. (b) of FIG. 14 illustrates an arrangement for bending a light beam by passing the light beam through a wedge prism. In a case where a beam of light for forming an image of the letter R is bended through reflection at the reflecting surface of a mirror as illustrated in (a) of FIG. 14, the image is inclined with respect to a plane (irradiation plane) perpendicular to the axis of the light beam. In a case where a light beam having a fixed width as in the optical unit 20 of each of the microscopes 1 and 100 of the present invention is bended through reflection at the reflecting surface of a mirror, the width direction of the light beam is undesirably changed. In this case, it is impossible to successfully control the thickness of a region illuminated with sheet light emitted by the illumination lens 26.

In contrast, in the microscope 1, a light beam having a fixed width passes through the wedge prism 50 to be bended without changes in its width direction.

Figure 15:
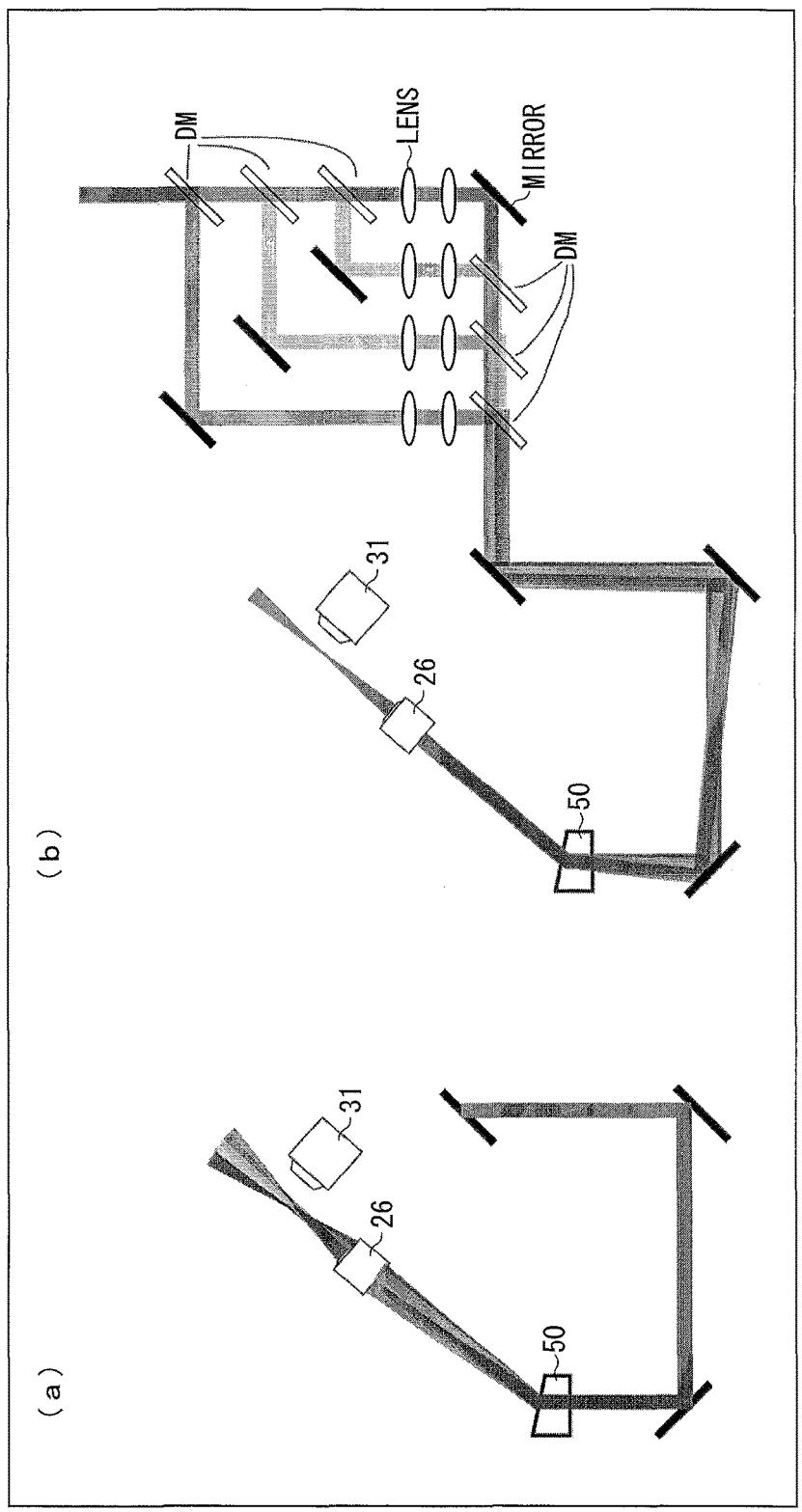
FIG. 15 shows diagrams each illustrating optical paths of light beams having different wavelengths which light beams are bended with use of a wedge prism in an optical unit.

FIG. 15 shows diagrams each illustrating optical paths of light beams having different wavelengths which light beams are bended with use of a wedge prism in an optical unit. (a) of FIG. illustrates how the mutually aligned optical paths of multispectral laser beams are changed when the multispectral laser beams pass through a wedge prism. (b) of FIG. 15 illustrates how the mutually varied optical paths of multispectral laser beams are changed when the multispectral laser beams pass through a wedge prism.

The optical unit 20 of the microscope 1 of the variation uses a wedge prism 50 to bend light beams. In such a case, since the wedge prism 50 has a refractive index that varies depending on the wavelength of light, when different laser beams having different wavelengths and having the same optical path are bended by being passed through the wedge prism 50, the optical paths of the laser beams having passed through the wedge prism 50 would be different from one another with respect to the wavelengths as illustrated in (a) of FIG. 15. In this case, sheet light emitted by the optical unit 20 undesirably forms an illuminated region having a large thickness.

The optical unit 20 is thus preferably arranged as illustrated in (b) of FIG. 15 such that light beams having different wavelengths and having different optical paths aligned with one another are first bended with use of DMs, mirrors, and lenses at angles predetermined in correspondence with respect to each wavelength so that the optical paths differ from one another in correspondence with respect to each wavelength and that the light beams are then bended with use of a wedge prism 50. This arrangement involves adjusting the optical paths of light beams with respect to each wavelength in advance with use of DMs, mirrors, and lenses so that the light beams having the different wavelengths which light beams have passed through the wedge prism will have optical paths aligned with one another.

EXAMPLE 1

Figure 16:
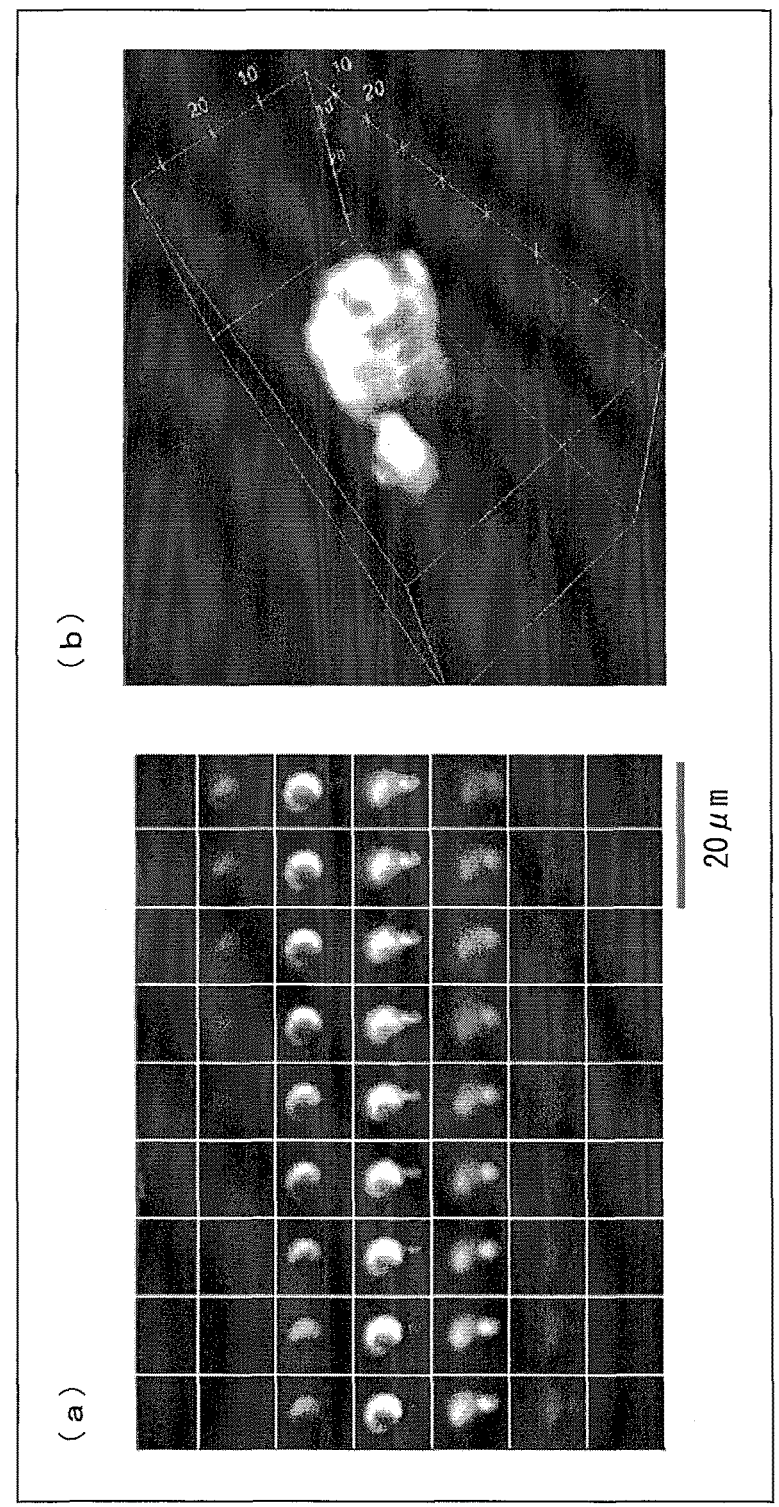
FIG. 16 illustrates an Example involving use of a microscope of the present invention.

FIG. 16 illustrates an Example involving use of a microscope of the present invention. (a) of FIG. 16 shows images of a budding yeast cell on different X'-Y planes which images were produced by scanning an observation plane along the Z' direction. (b) of FIG. 16 shows a three-dimensional image of the budding yeast cell.

The images of FIG. 16 are fluorescence images produced by irradiating, with sheet light, a budding yeast cell (Saccharomyces cerevisiae: mKate2/pESC-HIS/BY4741) clustered in the vicinity of the placement surface of the sample placement part while scanning the illuminated region along the first direction (Z' direction) in steps of 0.25 μm with use of the first stage 110 and with use of the CCD camera 35, capturing an image of fluorescence radiated from the sample.

The microscope of the present invention allows observation of a sample in the vicinity of the placement surface of the sample placement part (cover slip). The microscope successfully formed an image of the entire volume (approximately 6 μm in diameter) of a budding yeast cell in the vicinity of the placement surface as described above.

EXAMPLE 2

Figure 17:
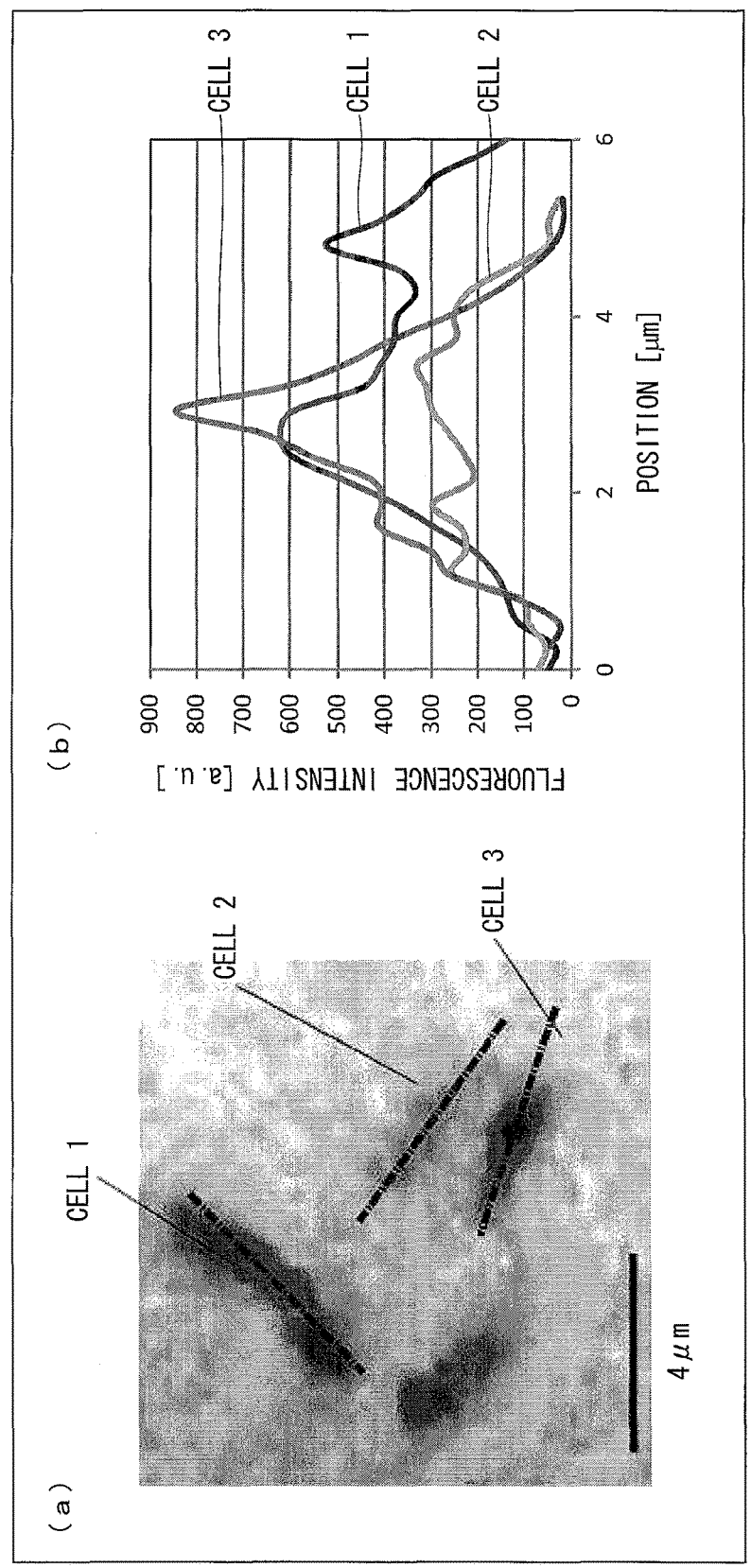
FIG. 17 illustrates an Example involving use of a microscope of the present invention.
Figure 18:
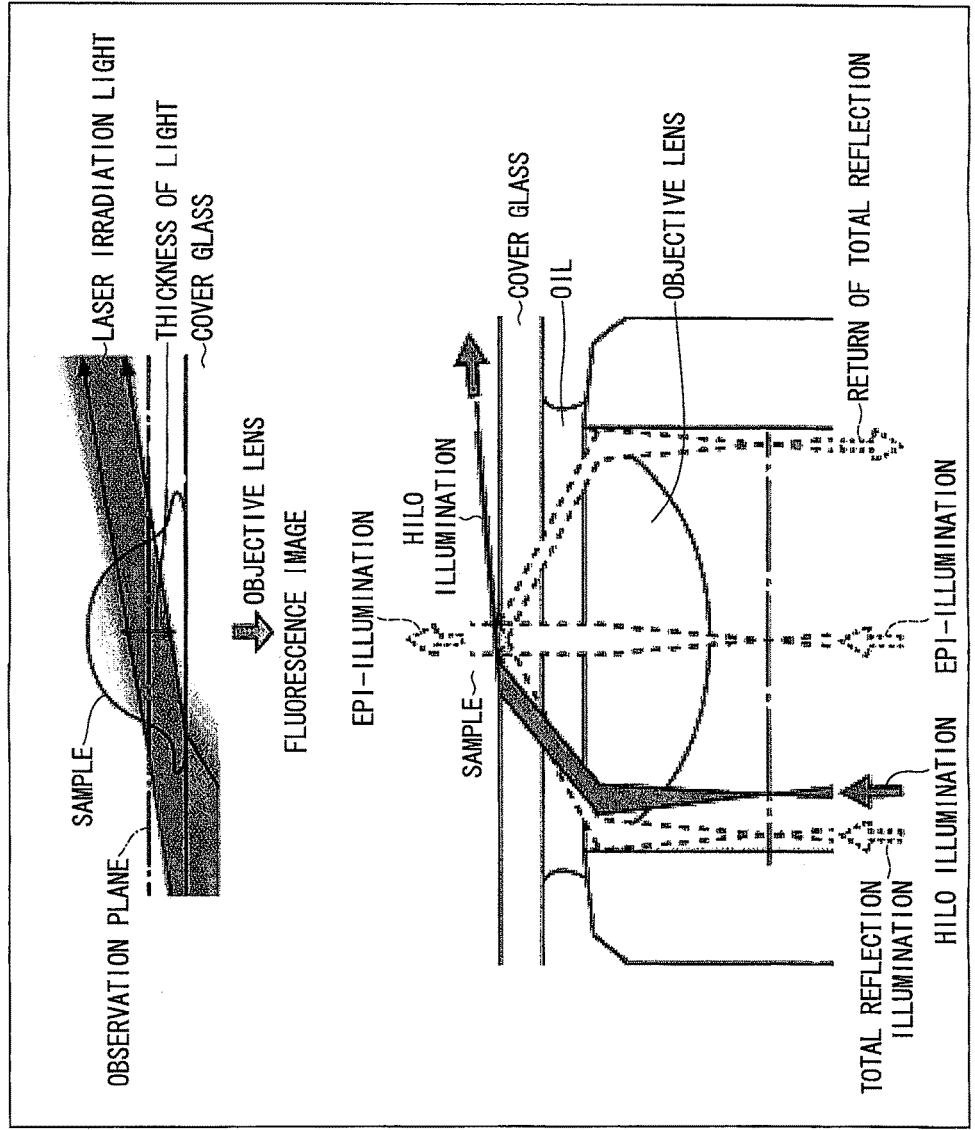
FIG. 18 shows diagrams each schematically illustrating a main configuration of an optical microscope based on a conventional highly inclined laminated optical sheet microscopy.
Figure 19:
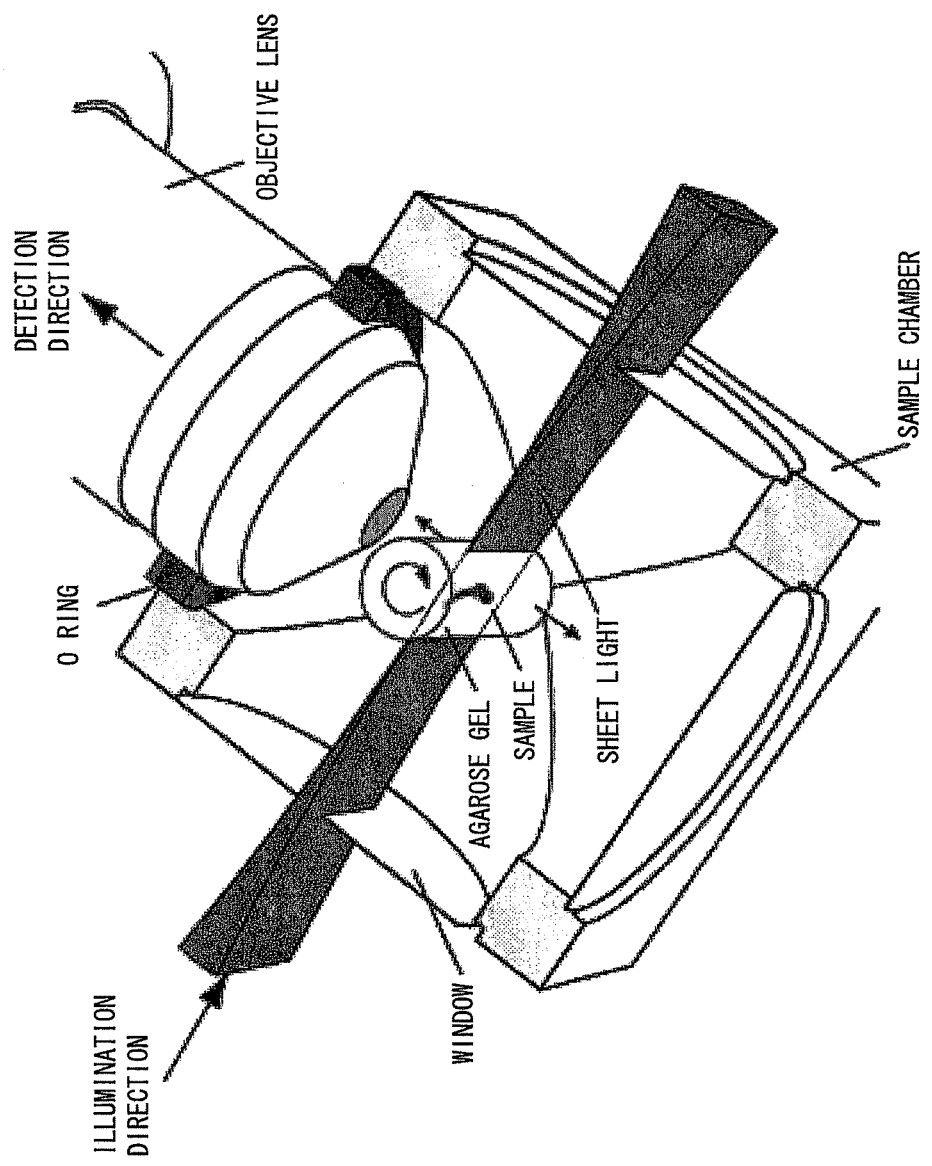
FIG. 19 is a diagram schematically illustrating a main configuration of a conventional SPIM.

FIG. 17 illustrates an Example involving use of a microscope of the present invention. (a) of FIG. 17 is a fluorescence image of *Escherichia coli*. (b) of FIG. 17 is a luminance profile for the fluorescence image of *Escherichia coli*.

The microscope of the present invention can include a lens with a large numerical aperture (for example, NA=1.1) as the observation lens 31, and thus allows observation at a high resolution.

Fluorescence imaging was carried out of an *Escherichia coli* strain (*E. coli*: SX4) that expresses an average of one fluorescent protein molecule per cell. A fluorescence image was produced in this observation example by fixing *Escherichia coli* to a cover slip having a low refractive index and irradiating the sample with 514-nm sheet light to excite the sample. This observation resulted in detection of two bright points of single-molecule fluorescence in the cell 1, no such bright point in the cell 2, and one such bright point in the cell 3 (see FIG. 17).

The present invention is not limited to the description of the embodiments above, and may be altered within the scope of the claims in various ways. Any embodiment based on a proper combination of technical means disclosed in different embodiments is also encompassed in the technical scope of the present invention.

INDUSTRIAL APPLICABILITY

The present invention allows observation of a sample at a high resolution at a single-molecule level which observation is free from restrictions such as the size of a sample. The present invention is therefore suitably applicable to development of new medicaments based on cells.

REFERENCE SIGNS LIST 1, 100 microscope
10 sample placement part
11 placement surface
12 sample
13 bottom face
20 optical unit
31 observation lens
40 fluid holding device
41 connection section
42 end face
43 transmission window
44 fluid holding section
110 first stage (focusing mechanism, focusing device)
120 second stage (focusing mechanism, focusing device)

The invention claimed is:

1. A microscope, comprising:
a sample placement part having a placement surface at which to place a sample and a face opposite to the placement surface;
an observation lens for receiving fluorescence from the sample; and
an optical unit configured to generate sheet light traveling in a direction substantially parallel to an observation plane of the observation lens, such that
the sheet light entering the sample placement part from the face opposite to the placement surface passes through the sample placement part to irradiate the sample, and
the fluorescence passes through the sample placement part toward the face opposite to the placement surface to be received by the observation lens.

2. The microscope according to claim 1, further comprising
a focusing mechanism for adjusting a relative positional relationship between the observation lens and the sample,
wherein
the focusing mechanism is configured to change the positional relationship along a first direction, which is substantially parallel to an optical axis of the observation lens, and a second direction and a third direction, which define the placement surface.

3. The microscope according to claim 1, further comprising
a fluid holding device for holding fluid between the observation lens and the sample placement part,
wherein:
the fluid holding device comprises:
a connection section for connection to the observation lens;
an end face adjacent to the face opposite to the placement surface;
a transmission window; and
a fluid holding section for holding fluid inside itself; and
in a state where the fluid holding device is connected to the observation lens, the end face is substantially parallel to the face opposite to the placement surface, the sheet light passes through the transmission window and then through the fluid holding section to irradiate the sample, and the fluorescence passes through the fluid holding section to be received by the observation lens.

4. The microscope according to claim 3,
wherein:
the observation lens is an immersion lens; and
the fluid holding section is filled with a liquid corresponding to the immersion lens.

5. The microscope according to claim 4,
wherein:
the fluid holding section is filled with water; and
the sample placement part has a refractive index of 1.28 to 1.38.

6. The microscope according to claim 1,
wherein
the observation plane and the placement surface form an angle within a range from 1 degree to 75 degrees.

7. The microscope according to claim 1,
wherein:
the optical unit comprises an optical surface plate having a surface on which one or more optical elements for generating the sheet light are disposed; and
the optical surface plate is oriented so that the surface of the optical surface plate is substantially parallel to the observation plane.

8. The microscope according to claim 7,
wherein:
the one or more optical elements comprise a light source, a light converging element, and a light distributing element; and
the one or more optical elements optionally further comprise a wedge prism.

9. A fluid holding device for holding fluid between an observation lens and a sample placement part, the sample placement part having a placement surface at which to place a sample to be observed and a face opposite to the placement surface,
the fluid holding device comprising:
a connection section for connection to the observation lens;
an end face adjacent the face opposite to the placement surface;
a transmission window; and
a fluid holding section for holding fluid inside itself,
in a state where the fluid holding device is connected to the observation lens, the end face being substantially parallel to the face opposite to the placement surface, the sheet light from an optical unit passing through the transmission window and then through the fluid holding section to irradiate the sample, and fluorescence from the sample passing through the fluid holding section to be received by the observation lens.

10. An optical unit for use in an upright microscope or inverted microscope,
the optical unit comprising
an optical surface plate having a surface on which one or more optical elements for generating sheet light are placed, the optical surface plate being oriented so that the surface of the optical surface plate is substantially parallel to an observation plane of an observation lens.

11. A microscope, comprising:

a sample placement part having a placement surface on which to place a sample and a face opposite to the placement surface;

an observation lens for receiving fluorescence from the sample; and an optical unit configured to generate sheet light having a thickness in a direction substantially parallel to an optical axis of the observation lens, such that the sheet light entering the sample placement part from the face opposite to the placement surface passes through the sample placement part to irradiate the sample, and the fluorescence passes through the sample placement part toward the face opposite to the placement surface to be received by the observation lens.

12. A microscope, comprising:

a sample placement part having a placement surface on which to place a sample and a face opposite to the placement surface;

an observation lens for receiving fluorescence from the sample; and an optical unit configured to irradiate the sample with sheet light in a direction substantially perpendicular to an optical axis of the observation lens, such that the sheet light entering the sample placement part from the face opposite to the placement surface passes through the sample placement part to irradiate the sample in the direction substantially perpendicular to the optical axis of the observation lens, and the fluorescence passes through the sample placement part toward the face opposite to the placement surface to be received by the observation lens.

* * * * *